(12) United States Patent
Matsumoto et al.

(10) Patent No.: US 11,952,447 B2
(45) Date of Patent: Apr. 9, 2024

(54) POLYMERIZABLE COMPOSITION FOR DENTAL MATERIAL, AND DENTAL MATERIAL OBTAINED FROM SAID COMPOSITION

(71) Applicant: MITSUI CHEMICALS, INC., Tokyo (JP)

(72) Inventors: Takuya Matsumoto, Ichihara (JP); Naoyuki Kakinuma, Ichihara (JP)

(73) Assignee: MITSUI CHEMICALS, INC., Tokyo (JP)

( * ) Notice: Subject to any disclaimer, the term of this patent is extended or adjusted under 35 U.S.C. 154(b) by 828 days.

(21) Appl. No.: 16/981,802

(22) PCT Filed: Mar. 28, 2019

(86) PCT No.: PCT/JP2019/013614
§ 371 (c)(1),
(2) Date: Sep. 17, 2020

(87) PCT Pub. No.: WO2019/189579
PCT Pub. Date: Oct. 3, 2019

(65) Prior Publication Data
US 2021/0017313 A1    Jan. 21, 2021

(30) Foreign Application Priority Data
Mar. 30, 2018 (JP) ................ 2018-068931

(51) Int. Cl.
C08F 220/14    (2006.01)
A61K 6/30      (2020.01)
C08K 3/36      (2006.01)

(52) U.S. Cl.
CPC ........... C08F 220/14 (2013.01); C08K 3/36 (2013.01)

(58) Field of Classification Search
None
See application file for complete search history.

(56) References Cited

U.S. PATENT DOCUMENTS

| | | | |
|---|---|---|---|
| 4,866,148 A * | 9/1989 | Geyer | G02B 1/043 523/108 |
| 4,873,269 A | 10/1989 | Nakazato | |
| 5,502,087 A * | 3/1996 | Tateosian | C08F 279/06 433/199.1 |
| 6,133,338 A * | 10/2000 | Kimura | C09J 4/00 524/521 |
| 6,196,843 B1 | 3/2001 | Kawaguchi et al. | |
| 8,192,673 B2 * | 6/2012 | Bowman | C08G 75/045 264/494 |
| 8,796,492 B2 * | 8/2014 | Saito | C07C 41/06 568/687 |
| 8,859,642 B2 * | 10/2014 | Miyamoto | C08F 2/24 524/533 |
| 8,962,709 B2 * | 2/2015 | Bowman | C08F 222/1025 522/42 |
| 9,114,079 B2 * | 8/2015 | Bublewitz | A61K 6/20 |
| 9,463,146 B2 * | 10/2016 | Fornof | C07C 69/604 |
| 9,532,929 B2 * | 1/2017 | Fornof | A61K 6/60 |
| 9,758,478 B2 * | 9/2017 | Fornof | C08F 290/067 |
| 9,907,733 B2 * | 3/2018 | Joly | A61K 6/30 |
| 11,116,702 B2 * | 9/2021 | Fik | A61C 5/50 |
| 2009/0118389 A1 * | 5/2009 | Abuelyaman | A61K 6/887 522/64 |
| 2013/0225699 A1 | 8/2013 | Bublewitz et al. | |
| 2016/0229800 A1 * | 8/2016 | Fornof | A61C 5/50 |

FOREIGN PATENT DOCUMENTS

| | | |
|---|---|---|
| JP | S56-92901 A | 7/1981 |
| JP | S57-102807 A | 6/1982 |
| JP | S62-149608 A | 7/1987 |
| JP | S63-35508 A | 2/1988 |
| JP | H4-34962 B2 | 6/1992 |
| JP | H11-335221 A | 12/1999 |
| JP | 2013-538837 A | 10/2013 |

OTHER PUBLICATIONS

International Search Report dated Jun. 11, 2019, by the Japanese Patent Office in corresponding International Publication No. PCT/JP2019/013614 and an English translation of the Report. (5 pages).
Written Opinion of the International Searching Authority dated Jun. 11, 2019, by the Japanese Patent Office in corresponding International Publication No. PCT/JP2019/013614 and an English translation of the Opinion. (14 pages).

* cited by examiner

*Primary Examiner* — Sanza L. McClendon
(74) *Attorney, Agent, or Firm* — BUCHANAN, INGERSOLL & ROONEY PC

(57) ABSTRACT

Provided are a polymerizable composition for a dental material that can yield cured molded bodies having superior mechanical strength, a molded body obtained by curing the composition, and a dental material including the molded body. A polymerizable composition for a dental material, the polymerizable composition containing: one selected from the group consisting of allyl compound (A) and an oligomer of allyl compound (A); and (meth)acrylate compound (B).

17 Claims, 1 Drawing Sheet

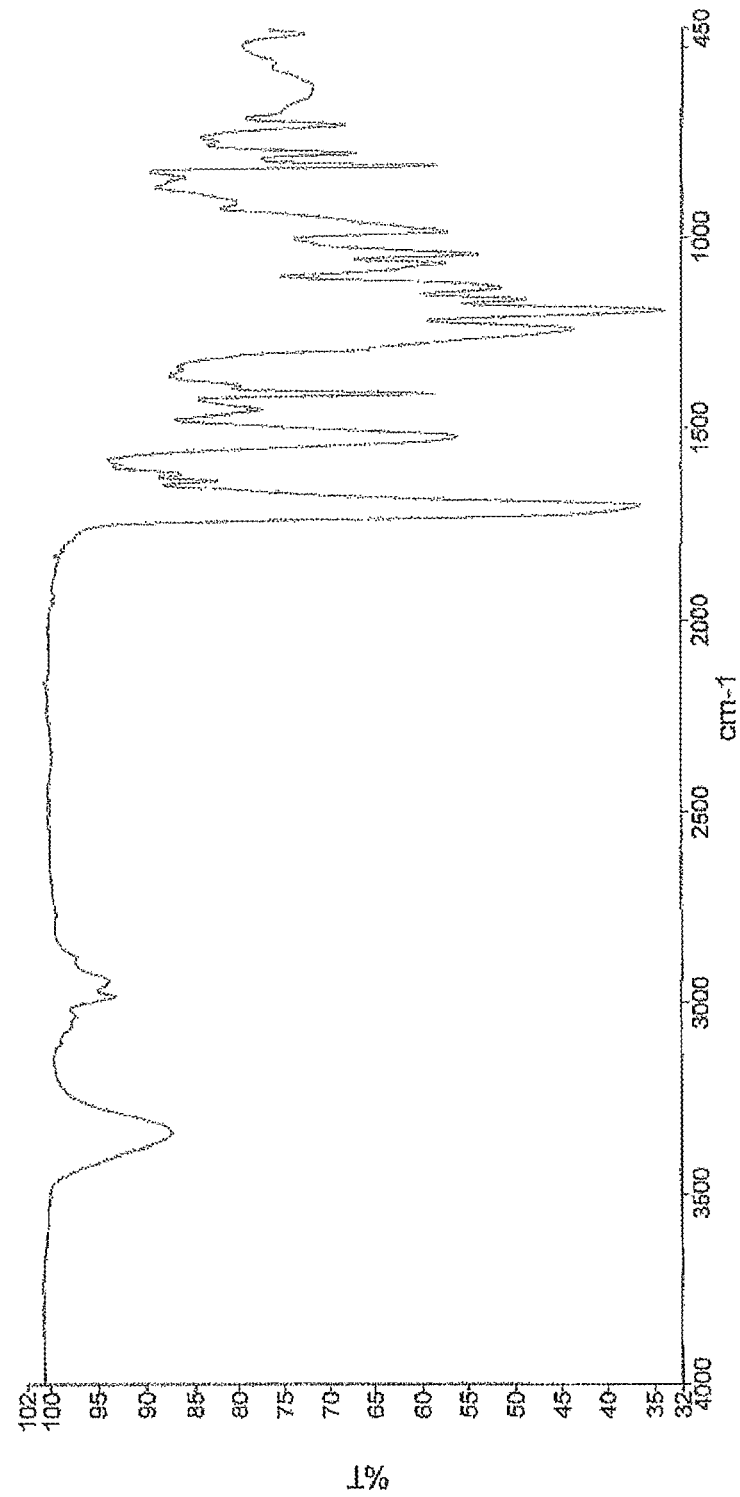

POLYMERIZABLE COMPOSITION FOR DENTAL MATERIAL, AND DENTAL MATERIAL OBTAINED FROM SAID COMPOSITION

TECHNICAL FIELD

The present invention relates to a novel polymerizable composition for a dental material, a molded body obtained by curing the polymerizable composition for a dental material, and a dental material including the molded body.

BACKGROUND ART

Composite resin, a representative example of compositions for a dental material, typically contains a monomer composition, a filler, a polymerization initiator, a polymerization inhibitor, a coloring substance, and so on. Regarding the weight ratio of components in composite resin, the highest is typically the weight of the filler and the second highest is the weight of the monomer composition, and the two components account for the most of the weight of composite resin. The monomer composition serves as a binder for the filler, and the monomer physical properties and the physical properties of a cured product of the monomer composition largely affect the physical properties and performance of composite resin containing the monomer composition and a cured product thereof.

For the monomer composition, compositions of radical-polymerizable polyfunctional methacrylate are used in most cases, from the viewpoints of the in vivo safety of the monomer and the mechanical strength, abrasion resistance, and so on of the cured product. A typical example of compositions of polyfunctional methacrylate is a composition containing 2,2-bis[4-(3-methacryloyloxy-2-hydroxypropoxy)phenyl]propane (hereinafter, referred to as Bis-GMA) or 2,2,4-trimethylhexamethylenebis(2-carbamoyloxyethyl) dimethacrylate (hereinafter, referred to as UDMA) as a primary component with triethylene glycol dimethacrylate (hereinafter, referred to as TEGDMA) blended for viscosity adjustment.

Repair of tooth loss with composite resin has long been used for dental treatment in clinical practice, and the range of uses of composite resin has been increasingly become wider. However, mechanical properties of cured products of composite resin are still insufficient, and application thereof to tooth crown materials or the like for sites to be exposed to high stress, such as molar teeth, is currently restricted, especially because of the poor strength.

Extended application of composite resin to such sites to be exposed to high stress has been recently strongly demanded from clinical practitioners, and it is an urgent task to develop composite resin having higher mechanical properties. As described above, the physical properties of a cured product of the monomer composition to be contained in composite resin largely affect the physical properties of a cured product of composite resin containing the monomer composition.

In view of this, an attempt has been made to enhance mechanical strength of cured products of polymerizable compositions for a dental material, including composite resin, by using a monomer alternative to Bis-GMA and UDMA, which are widely used as a primary component of monomer compositions.

For example, Patent Literature 1 discloses a composition for resins with use of a diallyl isophthalate (DAP) prepolymer and a diallyl isophthalate (DAP) monomer as primary components.

CITATION LIST

Patent Literature

Patent Literature 1: Japanese Patent Publication No. 4-034962

SUMMARY OF INVENTION

Technical Problem

As described above, it is needed for extension of the applicable range of polymerizable compositions for a dental material, including composite resin, to enhance mechanical properties of molded bodies obtained by curing a polymerizable composition for a dental material. In particular, composite resin for molar teeth is required to have even higher mechanical properties. However, molded bodies of the composition for resins in Patent Literature 1 have points to be improved with respect to mechanical properties.

In view of the above problems, an object of the present invention is to provide a polymerizable composition for a dental material that can yield cured molded bodies having superior mechanical strength, a molded body obtained by curing the composition, and a dental material including the molded body.

Solution to Problem

The present inventors diligently examined to find that a molded body obtained by curing a polymerizable composition for a dental material, the polymerizable composition containing a (meth)acrylate compound primarily used for a dental material and an allyl compound, exhibits high mechanical strength, thereby completing the present invention.

Specifically, the present invention is shown as follows.

[1] A polymerizable composition for a dental material, the polymerizable composition containing:

one selected from the group consisting of allyl compound (A) and an oligomer of allyl compound (A); and (meth)acrylate compound (B).

[2] The polymerizable composition for a dental material according to [1], wherein the mass ratio of allyl compound (A) to (meth)acrylate compound (B) is in the range of 0.05 or higher and lower than 1.0.

[3] The polymerizable composition for a dental material according to [1] or [2], wherein allyl compound (A) is a compound having an allyloxy group.

[4] The polymerizable composition for a dental material according to any one of [1] to [3], wherein allyl compound (A) includes compound (A1) represented by general formula (A1) below or compound (A2) represented by general formula (A2) below:

[Chem. 1]

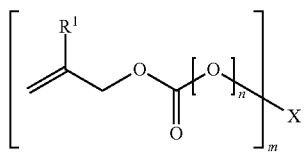
(A1)

wherein m is an integer of 2 to 8, each group $R^1$ is a hydrogen atom or a methyl group, groups $R^1$ are the same or different, n is an integer of 0 or 1, X is an m-valent $C_{2-100}$ hydrocarbon group optionally having a substituent and optionally containing a heteroatom,

[Chem. 2]

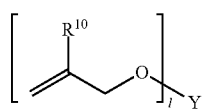
(A2)

wherein l is an integer of 1 to 8, each group $R^{10}$ is a hydrogen atom or a methyl group, groups $R^{10}$ are the same or different;

if l is 2 to 8, then Y is an l-valent $C_{2-100}$ hydrocarbon group optionally having a substituent and optionally containing a heteroatom; and if l is 1, then Y is a group represented by general formula (Y1) below:

[Chem. 3]

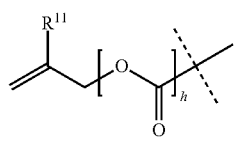
(Y1)

wherein $R^{11}$ is a hydrogen atom or a methyl group, h is an integer of 0 or 1, and the dashed line part represents a bonding position to the group in the parentheses in formula (A2).

[5] The polymerizable composition for a dental material according to [4], wherein allyl compound (A) includes compound (A1) represented by general formula (A1), and X in general formula (A1) is an m-valent $C_{2-100}$ chain hydrocarbon group optionally having a substituent and optionally containing a heteroatom, an m-valent $C_{5-16}$ alicyclic hydrocarbon group optionally having a substituent and optionally containing a heteroatom, or an m-valent $C_{6-50}$ aromatic hydrocarbon group optionally having a substituent and optionally containing a heteroatom.

[6] The polymerizable composition for a dental material according to [4], wherein allyl compound (A) includes compound (A1) represented by general formula (A1), and X in general formula (A1) is a group represented by any of general formulas (X1) to (X12) below:

[Chem. 4]

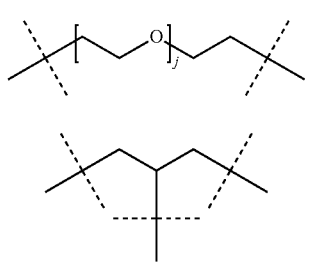
(X1)

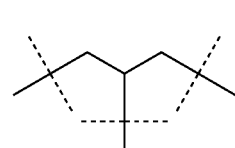
(X2)

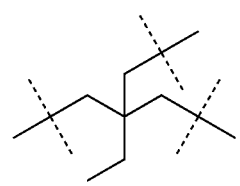
(X3)

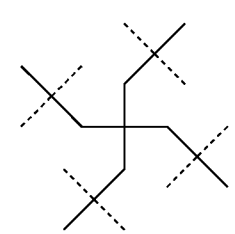
(X4)

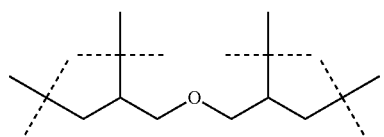
(X5)

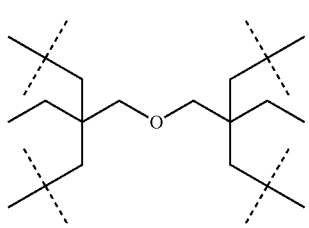
(X6)

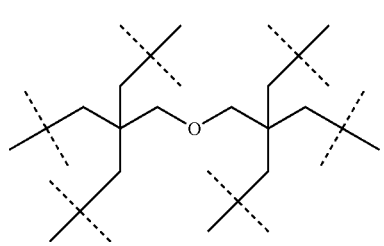
(X7)

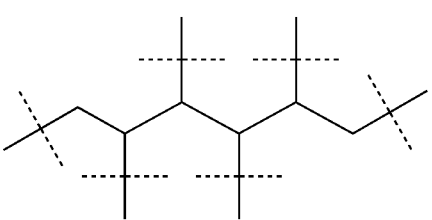
(X8)

-continued

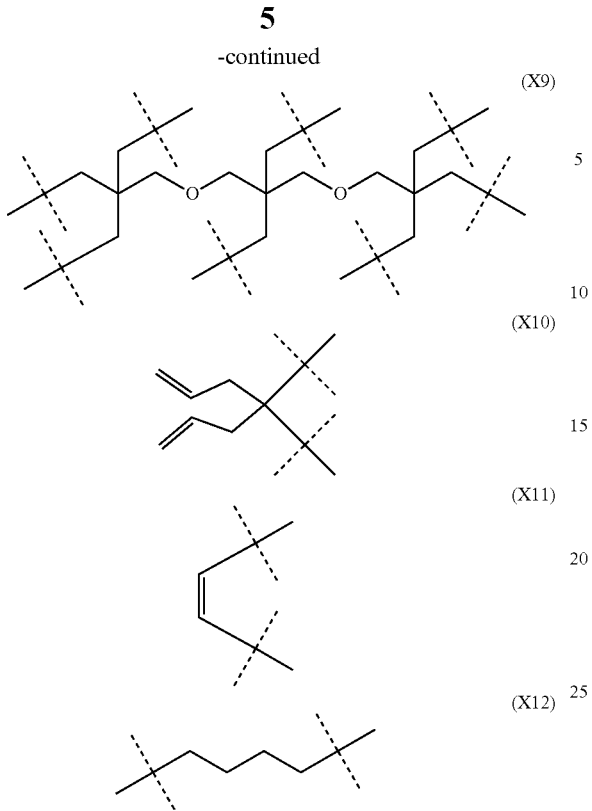

(X9)

(X10)

(X11)

(X12)

wherein j is an integer of 1 to 50, and each dashed line part in formulas (X1) to (X12) represents a bonding position to the group in the parentheses in formula (A1).

[7] The polymerizable composition for a dental material according to [4], wherein allyl compound (A) includes compound (A1) represented by general formula (A1), and X in general formula (A1) is an m-valent $C_{5-16}$ alicyclic hydrocarbon group optionally having a substituent and optionally containing a heteroatom.

[8] The polymerizable composition for a dental material according to [4], wherein allyl compound (A) includes compound (A1) represented by general formula (A1), and X in general formula (A1) is a group represented by any of general formulas (X13) to (X16) below:

[Chem. 5]

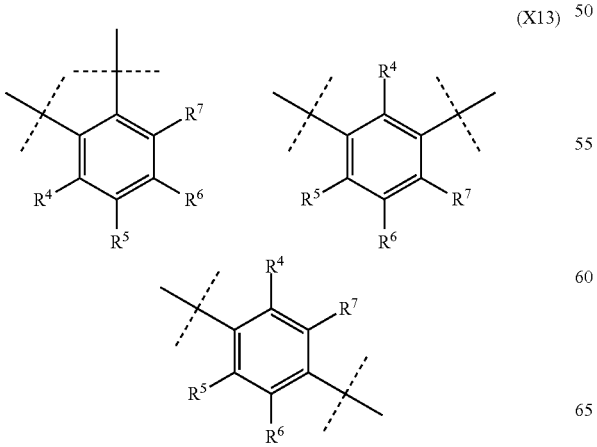

(X13)

-continued

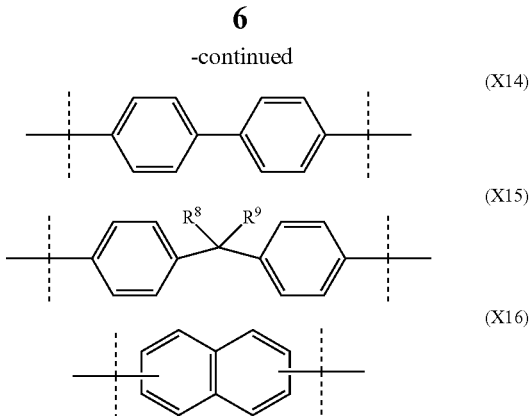

(X14)

(X15)

(X16)

wherein each dashed line part represents a bonding position to the group in the parentheses in formula (A1); $R^4$ to $R^7$ in formula (X13) are each independently a hydrogen atom, a halogen atom, or a $C_{1-20}$ aliphatic hydrocarbon group optionally containing a heteroatom, and the two dashed-lined bonding sites on the benzene ring are in any of ortho relationship, meta relationship, and para relationship; $R^8$ and $R^9$ in formula (X15) are each independently a hydrogen atom or a methyl group; and each of the two dashed-lined bonding sites on the naphthalene ring in formula (X16) is present at any of the eight bondable positions, and hydrogen atoms at positions other than the dashed-lined bonding sites on the naphthalene ring are each optionally replaced with another group.

[9] The polymerizable composition for a dental material according to [4], wherein allyl compound (A) includes compound (A2) represented by general formula (A2), and Y in general formula (A2) is an l-valent $C_{2-20}$ chain hydrocarbon group optionally having a substituent and optionally containing a heteroatom.

[10] The polymerizable composition for a dental material according to [4], wherein allyl compound (A) includes compound (A2) represented by general formula (A2), and Y in general formula (A2) is a group represented by general formula (Y1) or a group represented by any of general formulas (Y2) to (Y5) below:

[Chem. 6]

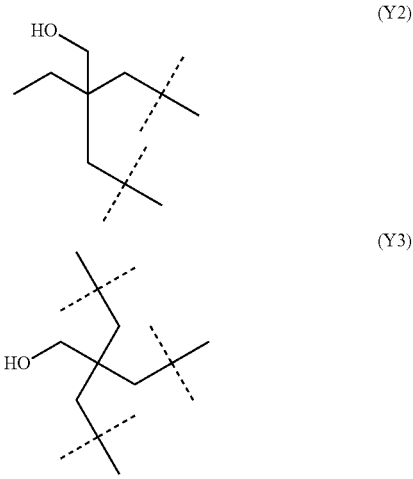

(Y2)

(Y3)

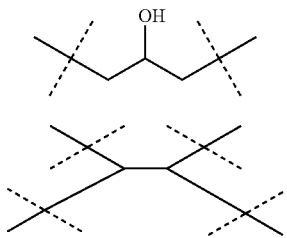
(Y4)

(Y5)

wherein each dashed line part represents a bonding position to the group in the parentheses in formula (A2).

[11] The polymerizable composition for a dental material according to any one of [1] to [10], wherein (meth) acrylate compound (B) includes (meth)acrylate compound (B-a) represented by general formula (2) below:

[Chem. 7]

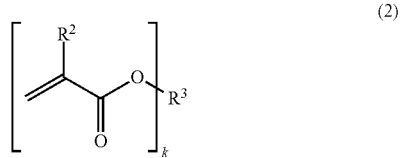
(2)

wherein k is an integer of 2 to 4, $R^3$ is a k-valent hydrocarbon group optionally containing a heteroatom, and $R^2$ is a hydrogen atom or a methyl group.

[12] The polymerizable composition for a dental material according to any one of [1] to [11], the polymerizable composition further containing a polymerization initiator.

[13] The polymerizable composition for a dental material according to [12], wherein the polymerization initiator contains a photopolymerization initiator.

[14] The polymerizable composition for a dental material according to any one of [1] to [13], the polymerizable composition further containing a filler.

[15] The polymerizable composition for a dental material according to any one of [1] to [14], wherein the viscosity of the polymerizable composition for a dental material at 65° C. is 1 to 300,000 mPa·s.

[16] The polymerizable composition for a dental material according to any one of [1] to [15], wherein the polymerizable composition is used as a dental composite resin.

[17] A molded body obtained by curing the polymerizable composition for a dental material according to any one of [1] to [16].

[18] A dental material including the molded body according to [17].

Advantageous Effects of Invention

Cured molded bodies having superior mechanical strength can be obtained from the polymerizable composition of the present invention for a dental material. Such molded bodies are useful as dental materials.

BRIEF DESCRIPTION OF DRAWING

FIG. 1 shows the IR spectrum of thiourethane acrylate (B-a1) obtained in Production Example.

DESCRIPTION OF EMBODIMENTS

Hereinafter, the polymerizable composition of the present invention for a dental material will be described in detail.

The polymerizable composition of the present invention for a dental material contains: one selected from the group consisting of allyl compound (A) and an oligomer of allyl compound (A); and (meth)acrylate compound (B).

Cured products of the polymerizable composition of the present invention for a dental material have superior mechanical strength. In particular, when the polymerizable composition of the present invention for a dental material is used for photopolymerization, a superior degree of polymerization is achieved, and thus superior mechanical strength is imparted to cured products. Since a superior degree of polymerization is achieved in using photopolymerization, adverse effects due to residual unpolymerized monomer can be more reliably prevented.

In the present invention, the phrase "superior mechanical strength is imparted" means at least either one of that a cured product of the polymerizable composition of the present invention for a dental material itself also has high mechanical strength (e.g., flexural strength, breaking energy) and that lowering of mechanical strength due to absorption of water is reduced.

Now, each component will be described.

[Allyl Compound (A)]

Allyl compound (A) in the present invention is a compound having one or more allyl groups.

Allyl compound (A) is preferably a compound having two or more allyl groups. Allyl compound (A) is preferably a compound having an allyloxy group, and more preferably a compound having two or more allyloxy groups. Examples of compounds having an allyloxy group include compounds having two or more allyloxycarbonyl groups (e.g., compound (A1) described later and represented by general formula (A1) below) and other compounds having an allyloxy group (e.g., compound (A2) described later and represented by general formula (A2) below).

Allyl compound (A) is preferably compound (A1) including two or more allyloxycarbonyl groups and represented by general formula (A1) below, or compound (A2) represented by general formula (A2) below (excluding compounds represented by general formula (A1) below).

[Chem. 8]

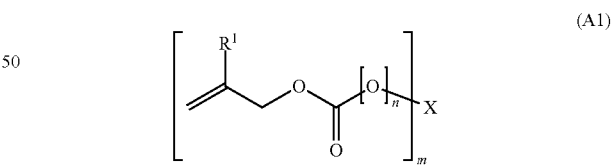
(A1)

In general formula (A1), m is an integer of 2 to 8, each group $R^1$ is a hydrogen atom or a methyl group, groups $R^1$ are the same or different, n is an integer of 0 or 1, X is an co-valent $C_{2-100}$ hydrocarbon group optionally having a substituent and optionally containing a heteroatom.

$R^1$ is preferably a hydrogen atom.

n is preferably 1 if X is an m-valent $C_{2-100}$ chain hydrocarbon group optionally having a substituent and optionally containing a heteroatom, which is described later, and is preferably 0 if X is an m-valent $C_{6-50}$ aromatic hydrocarbon group optionally having a substituent and optionally containing a heteroatom, which is described later.

m is preferably 2 to 6, more preferably 2 to 4, even more preferably 2 to 3, and particularly preferably 2.

Preferred as X in general formula (A1) above are an m-valent $C_{2-100}$ chain hydrocarbon group optionally having a substituent and optionally containing a heteroatom, an co-valent $C_{5-16}$ alicyclic hydrocarbon group optionally having a substituent and optionally containing a heteroatom, and an co-valent $C_{6-50}$ aromatic hydrocarbon group optionally having a substituent and optionally containing a heteroatom.

Examples of the $C_{2-100}$ chain hydrocarbon group that can be X include linear or branched saturated aliphatic hydrocarbon groups and linear or branched unsaturated aliphatic hydrocarbon groups. The number of carbon atoms of the chain hydrocarbon group is preferably 2 to 80, more preferably 2 to 40, and even more preferably 2 to 20.

Examples of the substituent that the chain hydrocarbon group may have include a cyclic alkyl group, an aralkyl group, a halogen atom, an alkoxy group, a carboxy group, an amino group, a thiol group, a hydroxy group, an aryl group, and a nitro group. If the substituent includes a hydrocarbon group, the hydrocarbon group may be any of linear, branched, and cyclic. The substituent is preferably a hydroxy group.

Examples of the heteroatom that the chain hydrocarbon group may contain include an oxygen atom, a nitrogen atom, a sulfur atom, and a phosphorus atom.

Examples of the chain hydrocarbon group containing a heteroatom include chain hydrocarbon groups including an ether bond and chain hydrocarbon groups including an ester bond.

The m-valent $C_{2-100}$ chain hydrocarbon group optionally having a substituent and optionally containing a heteroatom that can be X is preferably a chain hydrocarbon group optionally containing a heteroatom and represented by any of general formulas (X1) to (X12) below.

[Chem. 9]

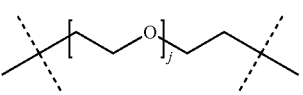
(X1)

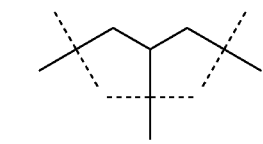
(X2)

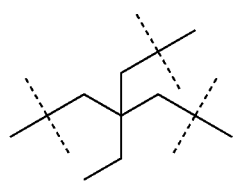
(X3)

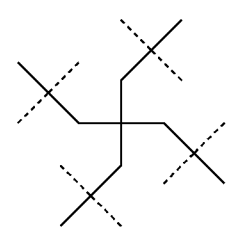
(X4)

-continued

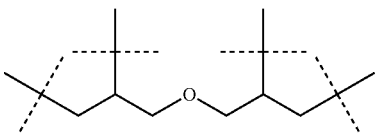
(X5)

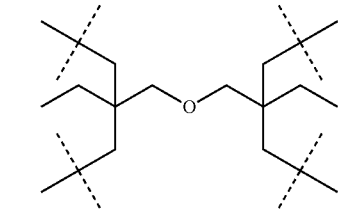
(X6)

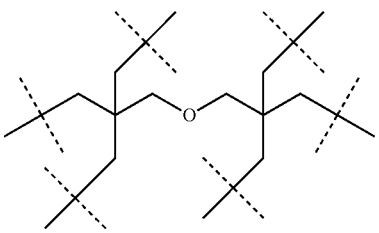
(X7)

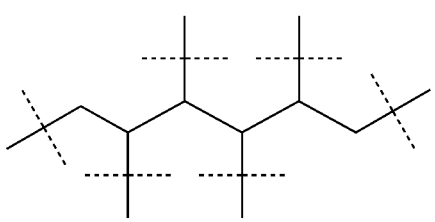
(X8)

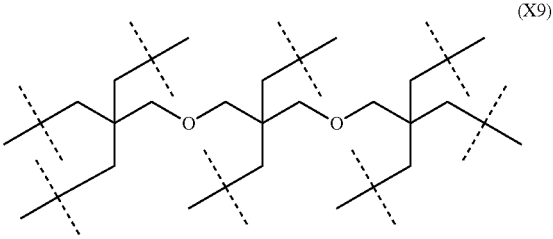
(X9)

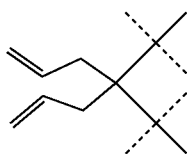
(X10)

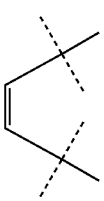
(X11)

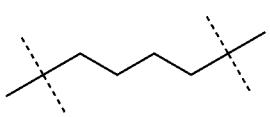
(X12)

In formula (X1), j is an integer of 1 to 50; and each dashed line part in formulas (X1) to (X12) represents a bonding position to the group in the parentheses in formula (A1). The group represented by formula (X1) is preferred among the groups represented by formulas (X1) to (X12). j in formula (X1) is preferably 1 to 30, more preferably 1 to 15, even more preferably 1 to 10, furthermore preferably 1 to 5, and particularly preferably 1.

Examples of the $C_{5-16}$ alicyclic hydrocarbon group that can be X, in the case of m=2, include a cyclopentylene group, a cyclohexylene group, a cycloheptylene group, a cyclooctylene group, a cyclononylene group, a cyclodecylene group, a cycloundecylene group, a cyclododecylene group, a spiro[4.5]decylene group, a spiro[5.5] undecylene group, a norbornylene group, a bornylene group, a tricyclodecylene group, an adamantylene group, an oxonylene group, and a tetrahydropyranylene group.

Examples of the substituent that the alicyclic hydrocarbon group may have include an alkyl group, an aralkyl group, a halogen atom, a linear, branched, or cyclic alkoxy group, a carboxy group, an amino group, a thiol group, a hydroxy group, an aryl group, and a nitro group. If the substituent includes a hydrocarbon group, the hydrocarbon group may be any of linear, branched, and cyclic.

Examples of the heteroatom that the alicyclic hydrocarbon group may include an oxygen atom, a nitrogen atom, a sulfur atom, and a phosphorus atom.

Examples of the alicyclic hydrocarbon group containing a heteroatom include alicyclic hydrocarbon group including an ether bond and alicyclic hydrocarbon groups including an ester bond.

Examples of the aromatic hydrocarbon group that can be X in the case of m=2 include a phenylene group, a biphenylene group, a naphthylene group, a bisphenylene group, and a heteroarylene group.

Examples of the substituent that the aromatic hydrocarbon group may include an alkyl group, a halogen atom, a hydroxy group, and an alkoxy group. If the substituent includes a hydrocarbon group, the hydrocarbon group may be any of linear, branched, or cyclic.

Examples of the heteroatom that the aromatic hydrocarbon group may include an oxygen atom, a nitrogen atom, a sulfur atom, and a phosphorus atom.

Examples of the aromatic hydrocarbon group containing a heteroatom include a thiophenylene group and a pyridylene group.

The m-valent $C_{6-50}$ aromatic hydrocarbon group optionally having a substituent and optionally containing a heteroatom that can be X is preferably an aromatic hydrocarbon group optionally having a substituent and optionally containing a heteroatom, wherein the aromatic hydrocarbon group is represented by any of general formulas (X13) to (X16) below.

[Chem. 10]

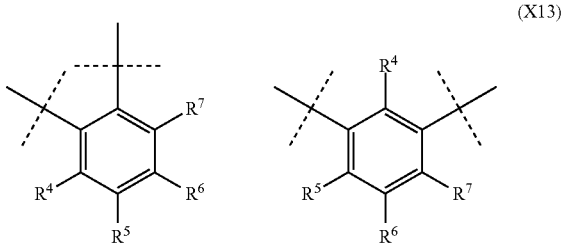

(X13)

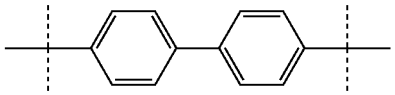

(X14)

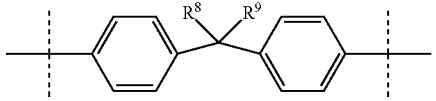

(X15)

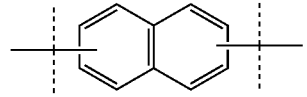

(X16)

In formulas (X13) to (X16), each dashed line part represents a bonding position to the group in the parentheses in formula (A1); $R^4$ to $R^7$ in formula (X13) are each independently a hydrogen atom, a halogen atom, or a $C_{1-20}$ aliphatic hydrocarbon group optionally containing a heteroatom, and the two dashed-lined bonding sites on the benzene ring are in any of ortho relationship, meta relationship, and para relationship; $R^8$ and $R^9$ in formula (X15) are each independently a hydrogen atom or a methyl group; each of the two dashed-lined bonding sites on the naphthalene ring in formula (X16) is present at any of the eight bondable positions, and hydrogen atoms at positions other than the dashed-lined bonding sites on the naphthalene ring are each optionally replaced with another group.

An allyl carbonate compound of polyhydric alcohol is a preferred mode of compound (A1) including two or more allyloxycarbonyl groups. Examples of such allyl carbonate compounds of polyhydric alcohol include bis(allyl carbonate) compounds of diol, tris(allyl carbonate) compounds of triol, tetra(allyl carbonate) compounds of tetraol, hexa(allyl carbonate) compounds of hexaol, octa(allyl carbonate) compounds of octaol, and allyl carbonate compounds of mixed polyol consisting of a mixture of these polyols.

A preferred bis(allyl carbonate) compound is, for example, bis(allyl carbonate) compound (A11) of at least one diol (a1) selected from the group consisting of diethylene glycol, dipropylene glycol, triethylene glycol, tetraethylene glycol, 1,3-propanediol, 1,4-butanediol, 1,5-pentanediol, 1,6-hexanediol, neopentyl glycol, 3-methyl-1,5-pentanediol, 2-methyl-2-ethyl-1,3-propanediol, 2,2-diethyl-1,3-propanediol, 2,2,4-trimethyl-1,3-pentanediol, 1,4-dimethylolcyclohexane, and 4,8-bis(hydroxymethyl)-[5.2.1.02,6]tricyclodecane.

A preferred tris(allyl carbonate) compound is, for example, tris(allyl carbonate) compound (A12) of at least one triol (a2) selected from the group consisting of glycerol, trimethylolpropane, and tris(hydroxyethyl) isocyanurate.

A preferred tetra(allyl carbonate) compound is, for example, tetra(allyl carbonate) compound (A13) of at least one tetraol (a3) selected from the group consisting of pentaerythritol, diglycerol, and ditrimethylolpropane.

A preferred hexa(allyl carbonate) compound is, for example, hexa(allyl carbonate) compound (A14) of at least one hexaol (a4) selected from the group consisting of dipentaerythritol and hexane-1,2,3,4,5,6-hexol.

A preferred octa(allyl carbonate) compound is, for example, octa(allyl carbonate) compounds (A15) of octaol (a5) of tripentaerythritol.

A preferred (allyl carbonate) compound of mixed polyol is, for example, (allyl carbonate compound) (A16)) of at least one mixed polyol selected from the group consisting of:

mixed polyol (a11) of diol (a1) and at least one tri- or higher-hydric polyol selected from the group consisting of triol (a2), tetraol (a3), hexaol (a4), and octaol (a5); mixed polyol (a12) of triol (a2) and at least one tetra- or higher-hydric polyol selected from the group consisting of tetraol (a3), hexaol (a4), and octaol (a5);

mixed polyol (a13) of tetraol (a3) and at least one penta- or higher-hydric polyol selected from the group consisting of hexaol (a4) and tripentaerythritol (a5); and mixed polyol (a14) with at least one hexa- or higher-hydric polyol selected from the group consisting of hexaol (a4) and octaol (a5).

Preferred as bis(allyl carbonate) compound (A11) are a bis(allyl carbonate) compound of diethylene glycol and a bis(allyl carbonate) compound of a mixture of diethylene glycol and neopentyl glycol, because cured molded bodies to be obtained have high mechanical strength.

Preferred as (allyl carbonate compound) (A15) of mixed polyol are a poly(allyl carbonate) compound of a mixture of diethylene glycol and tris(hydroxyethyl) isocyanurate, a poly(allyl carbonate) compound of a mixture of diethylene glycol and trimethylolpropane, a poly(allyl carbonate) compound of a mixture of diethylene glycol and pentaerythritol, and a poly(allyl carbonate) compound of mixture of diethylene glycol, neopentyl glycol and pentaerythritol, because cured molded bodies to be obtained have high mechanical strength.

An aryl alcohol ester compound of aromatic polycarboxylic acid is another preferred mode of compound (A1) including two or more allyloxycarbonyl groups.

Examples of such aryl alcohol ester compounds of aromatic polycarboxylic acid include at least one diallyl phthalate compound (a6) selected from the group consisting of diallyl isophthalate, diallyl terephthalate, and diallyl orthophthalate.

An example of another preferred mode of compound (A1) including two or more allyloxycarbonyl groups is a compound formed through transesterification of the above-mentioned aryl alcohol ester compound of aromatic polycarboxylic acid and a polyhydric alcohol.

Examples of such compounds include:

diallyl ester compounds obtained through transesterification reaction of diallyl phthalate compound (a6) and at least one diol (a15) selected from the group consisting of ethylene glycol, diethylene glycol, dipropylene glycol, triethylene glycol, tetraethylene glycol, 1,2-propanediol, 1,3-propanediol, 1,4-butanediol, 1,5-pentanediol, 1,6-hexanediol, neopentyl glycol, 3-methyl-1,5-pentanediol, 2-methyl-2-ethyl-1,3-propanediol, 2,2-diethyl-1,3-propanediol, 2,2,4-trimethyl-1,3-pentanediol, and 1,4-dimethylolcyclohexane; and polyallyl ester compounds obtained through transesterification reaction of diallyl phthalate compound (a6) and at least one polyol (a7) selected from the group consisting of glycerol, trimethylolpropane, tris(hydroxyethyl) isocyanurate, pentaerythritol, diglycerol, ditrimethylolpropane, dipentaerythritol, hexane-1,2,3,4,5,6-hexol, and tripentaerythritol.

Still other preferred modes of compound (A1) including two or more allyloxycarbonyl groups are, for example, an allyl ester compound, an allyl carbonate compound, and a compound having an allyl carbonate group and an allyl ester group, each obtained through transesterification reaction of a mixture of: at least one dialkyl phthalate selected from the group consisting of dialkyl isophthalates having $C_{1-3}$ alkyl groups, dialkyl terephthalates having $C_{1-3}$ alkyl groups, and dialkyl orthophthalates having $C_{1-3}$ alkyl groups; allyl alcohol; diallyl carbonate; and diol (a15) or polyol (a7).

Compound (A1) including two or more allyloxycarbonyl groups may be a mixture of an allyl carbonate compound of polyhydric alcohol and an aryl alcohol ester compound of aromatic polycarboxylic acid or a product of transesterification of an aryl alcohol ester of aromatic polycarboxylic acid and a polyhydric alcohol. Also acceptable is a product of transesterification of at least a part of an aryl alcohol ester compound of aromatic polycarboxylic acid with a polyhydric alcohol.

Examples of such mixtures include:

(i) a mixture of diallyl terephthalate and a bis(allyl carbonate) compound of diethylene glycol;

(ii) an allyl ester compound obtained through transesterification reaction of a mixture of diallyl terephthalate and propylene glycol;

(iii) a mixture of the allyl ester compound of (ii) and a bis(allyl carbonate) compound of diethylene glycol;

(iv) a mixture of an allyl ester compound, an allyl carbonate compound, and a compound having an allyl ester group and an allyl carbonate group, the mixture obtained through transesterification reaction of a mixture of dimethyl terephthalate, allyl alcohol, diallyl carbonate, and diethylene glycol; and (v) a mixture of the mixture obtained in (iv) and a bis(allyl carbonate) compound of diethylene glycol.

[Chem. 11]

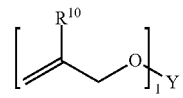

(A2)

In formula (A2), l is an integer of 1 to 8, each group $R^{10}$ is a hydrogen atom or a methyl group, groups $R^{10}$ are the same or different;

if l is 2 to 8, then Y is an l-valent $C_{2-100}$ hydrocarbon group optionally having a substituent and optionally containing a heteroatom.

If l is 1, then Y is a group represented by general formula (Y1) below:

[Chem. 12]

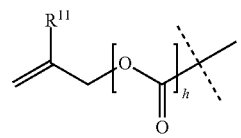

(Y1)

In formula (Y1), $R^{11}$ is a hydrogen atom or a methyl group, h is an integer of 0 or 1, and the dashed line part represents a bonding position to the group in the parentheses in formula (A2).

$R^{10}$ is preferably a hydrogen atom.

l is preferably 1, or 2 to 6, more preferably 1, or 2 to 4, even more preferably 1, or 2 to 3, and particularly preferably 1 or 2.

Preferred as Y if l is 2 to 8 in general formula (A2) above are an l-valent $C_{2-100}$ chain hydrocarbon group optionally having a substituent and optionally containing a heteroatom, an l-valent $C_{5-16}$ alicyclic hydrocarbon group optionally having a substituent and optionally containing a heteroatom, and an l-valent $C_{6-50}$ aromatic hydrocarbon group optionally having a substituent and optionally containing a heteroatom. Among them, the chain hydrocarbon group is preferred as Y.

Examples of the $C_{2-100}$ chain hydrocarbon group that can be Y in general formula (A2) above include the examples of the above-described $C_{2-100}$ chain hydrocarbon group that can be X in general formula (A1). The number of carbon atoms of the chain hydrocarbon group that can be Y is preferably 2 to 80, more preferably 2 to 40, and even more preferably 2 to 20.

Examples of the substituent that the chain hydrocarbon group as Y may have include those that the above-described $C_{2-100}$ chain hydrocarbon group that can be X in general formula (A1) may have. The substituent is preferably a hydroxy group.

Examples of the heteroatom that the chain hydrocarbon group as Y may include and the chain hydrocarbon group including the heteroatom include those described above for X in general formula (A1).

Y in general formula (A2) is preferably the group represented by general formula (Y1) or a group represented by any of general formulas (Y2) to (Y5) below.

[Chem. 13]

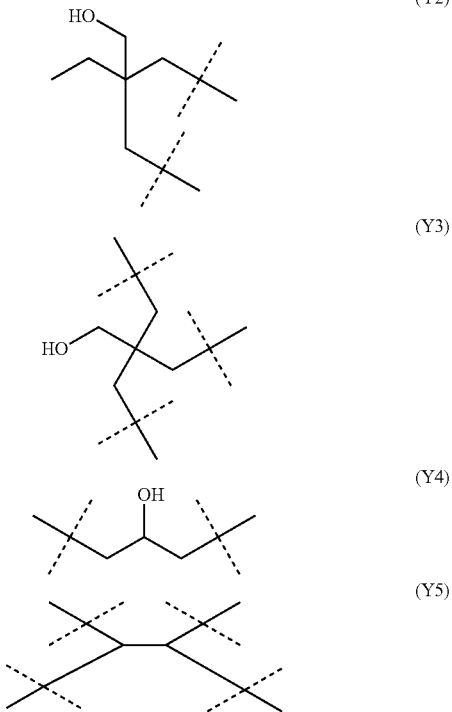

In formulas (Y2) to (Y5), each dashed line part represents a bonding position to the group in the parentheses in formula (A2).

Examples of the $C_{5-16}$ alicyclic hydrocarbon group that can be Y include the examples of the above-described $C_{5-16}$ alicyclic hydrocarbon group that can be X in general formula (A1).

Examples of the substituent that the alicyclic hydrocarbon group as Y may have include those that the above-described $C_{5-16}$ alicyclic hydrocarbon group that can be X in general formula (A1) may have.

Examples of the heteroatom that the alicyclic hydrocarbon group as Y may include and the alicyclic hydrocarbon group including the heteroatom include those described above for X in general formula (A1).

Examples of the $C_{6-50}$ aromatic hydrocarbon group that can be Y include the examples of the above-described $C_{5-16}$ aromatic hydrocarbon group that can be X in general formula (A1).

Examples of the substituent that the aromatic hydrocarbon group as Y may have include those that the above-described $C_{6-50}$ aromatic hydrocarbon group that can be X in general formula (A1) may have.

Examples of the heteroatom that the aromatic hydrocarbon group as Y may include and the aromatic hydrocarbon group including the heteroatom include those described above for X in general formula (A1).

In formula (Y1), $R^{11}$ is preferably a hydrogen atom, and h is preferably 1.

Especially in using for photopolymerization, allyl compound (A) is preferably one or more selected from the group consisting of diallyl phthalate (DAP), diethylene glycol bisallyl carbonate (BAC), and diallyl carbonate (DAC), because high degree of polymerization is achieved and thereby high mechanical strength is successfully provided.

One type of allyl compound (A) may be used singly, and two or more types of allyl compound (A) may be mixed for use.

[Oligomer of Allyl Compound (A)]

An oligomer of allyl compound (A) may be used for the polymerizable composition of the present invention for a dental material, in place of allyl compound (A), or together with allyl compound (A). An oligomer of allyl compound (A) refers to a di- to decamer consisting of molecules of allyl compound (A) linked through reaction of carbon-carbon double bonds included in the molecules of allyl compound (A). Oligomers of allyl compound (A) can be obtained from allyl compound (A) by using a common production method, and can be produced with adjustment of the amount of a catalyst and so on.

The content of allyl compound (A) or an oligomer thereof is not limited to particular values, but preferably 0.01 to 25% by mass and more preferably 3 to 16% by mass to the total mass of the polymerizable composition for a dental material.

The mass ratio of allyl compound (A) to (meth)acrylate compound (B) is not limited to particular values, but preferably 0.01 or higher and 1.1 or lower, more preferably 0.05 or higher and lower than 1.0, and even more preferably 0.1 or higher and 0.8 or lower, for the balance between mechanical strength and handleability as a dental material.

[(Meth)Acrylate Compound (B)]

In addition to allyl compound (A), (meth)acrylate compound (B) is contained in the polymerizable composition of the present invention for a dental material. (Meth)acrylate compound (B) is a compound having one or more (meth) acryl groups. In the present invention, a (meth)acrylate compound refers to an acrylate compound or a methacrylate compound.

(Meth)acrylate compound (B) preferably includes two or more (meth)acryl groups, and is more preferably acrylate compound (B-a) represented by general formula (2) below.

[Chem. 14]

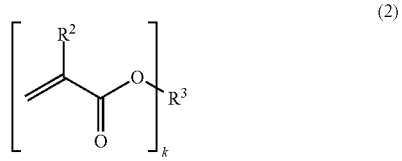

(2)

In formula (2), k represents an integer of 2 to 4, $R^3$ represents a k-valent hydrocarbon group optionally containing a heteroatom, and $R^2$ represents a hydrogen atom or a methyl group.

The hydrocarbon group as $R^3$ may be, for example, a chain hydrocarbon group (which may be a linear or branched aliphatic group or a saturated or unsaturated aliphatic group), an alicyclic hydrocarbon group, or an aromatic hydrocarbon group.

The number of carbon atoms of the hydrocarbon group as $R^3$ may be, for example, 1 to 200, and is preferably 1 to 150, more preferably 1 to 100, even more preferably 1 to 50, and furthermore preferably 1 to 30.

Examples of the heteroatom that the hydrocarbon group as $R^3$ optionally contains include an oxygen atom, a nitrogen atom, a sulfur atom, and a phosphorus atom. It is preferable that a sulfur atom and/or a nitrogen atom be contained as the heteroatom.

$R^3$ is preferably a hydrocarbon group having a urethane bond.

$R^2$ may be any of a hydrogen atom and a methyl group, and is preferably a hydrogen atom.

The viscosity of (meth)acrylate compound (B) at 65° C. is, for example, preferably 1 to 50000 mPa·s, more preferably 1 to 20000 mPa·s, even more preferably 1 to 5000 mPa·s, and particularly preferably 1 to 3000 mPa·s. The viscosity is a value obtained in measurement with an E-type viscometer at 65° C.

The molecular weight of (meth)acrylate compound (B) is preferably 80 to 3000, more preferably 150 to 2500, and even more preferably 200 to 2000. Because molecular weight lower than these ranges results in low boiling point, employing the above lower limit value is preferred for operability in preparing the polymerizable composition for a dental material. Molecular weight higher than those ranges tends to give higher viscosity, and hence employing the above upper limit value is preferred for operability in preparing the polymerizable composition for a dental material.

Known (meth)acrylate compounds may be used as (meth) acrylate compound (B). Examples thereof include (meth) acrylates having a urethane bond, (meth)acrylates having a divalent oxyalkylene group, and (meth)acrylates having a cyclic structure (e.g., methacrylate (B3-6) described later), and (meth)acrylates having a urethane bond are preferred because high toughness and high rigidity are successfully achieved in combination.

A reaction product of a compound having an isocyanate group and a hydroxy (meth)acrylate compound having one or more polymerizable groups may be used as a (meth) acrylate having a urethane bond.

Because urethane (meth)acrylates enable achievement of high toughness and high rigidity in combination and provide cured molded bodies having high mechanical properties, (meth)acrylates (B1), (B2), and (B3-5) below are each a preferred mode. Among them, (meth)acrylates (B2) and (B3-5), which are thiourethane (meth)acrylates, are each a more preferred mode.

[(Meth)Acrylate (B1)]

(Meth)acrylate (B1) is a urethane urea-type (meth)acrylate as a reaction product of a diamine, an iso(thio)cyanate compound having two or more iso(thio)cyanato groups, and a hydroxy (meth)acrylate having one or more polymerizable groups.

The iso(thio)cyanate compound is a compound having two or more iso(thio)cyanato groups. Herein, an iso(thio) cyanato group refers to an isocyanato group (—NCO) or an isothiocyanato group (—NCS), and an iso(thio)cyanate compound refers to an isocyanate compound or an isothiocyanate compound.

For the iso(thio)cyanate compound, those described later for (meth)acrylate (B2) may be used.

For the isocyanate compound, those described later for (meth)acrylate (B2) may be used.

The hydroxy (meth)acrylate compound having one or more polymerizable groups is a compound including: at least one polymerizable group selected from a methacryloyl group and an acryloyl group; and a hydroxy group.

For the hydroxy acrylate compound having one or more polymerizable groups, those described later for (meth)acrylate (B2) may be used.

Urethane urea-type (meth)acrylate (B1) in the present invention is obtained by reacting a diamine, an iso(thio) cyanate compound, and a hydroxy (meth)acrylate compound as described above, and the reaction may be performed by using a known method or a method according to a known method.

[(Meth)Acrylate (B2)]

(Meth)acrylate (B2) is a reaction product of a thiol compound having three or more mercapto groups, an iso (thio)cyanate compound having two or more iso(thio)cyanato groups, and a hydroxy (meth)acrylate compound having one or more polymerizable groups.

The thiol compound having three or more mercapto groups refers to a compound having three or more mercapto groups, and being a thiol compound.

An example of the thiol compound having three or more mercapto groups is a compound selected from the group consisting of aliphatic polythiol compounds, aromatic polythiol compounds, and heterocyclic polythiol compounds.

There is no limitation to the thiol compound having three or more mercapto groups applicable to the present embodiment, but preferably used for the advantageous effects of the present invention are one or two or more compounds selected from the group consisting of trimethylolpropane tris(3-mercaptopropionate), pentaerythritol tetrakis(2-mercaptoacetate), pentaerythritol tetrakis(3-mercaptopropionate), 4-mercaptomethyl-1,8-dimercapto-3,6-dithiaoctane, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, and 1,1,3,3-tetrakis(mercaptomethylthio) propane.

Examples of the iso(thio)cyanate compound include aliphatic polyisocyanate compounds, alicyclic polyisocyanate compounds, aromatic polyisocyanate compounds, heterocyclic polyisocyanate compounds, aliphatic polyisothiocyanate compounds, alicyclic polyisothiocyanate compounds, aromatic polyisothiocyanate compounds, sulfur-containing heterocyclic polyisothiocyanate compounds, and modified product of them.

Examples of the isothiocyanate compound include:
aliphatic polyisothiocyanate compounds such as hexamethylene diisothiocyanate;
alicyclic polyisothiocyanate compounds such as isophorone diisothiocyanate;
aromatic polyisothiocyanate compounds such as tolylene diisothiocyanate; and
sulfur-containing heterocyclic polyisothiocyanate compounds such as 2,5-diisothiocyanatothiophene.

The isocyanate compound is not limited to a particular isocyanate compound, but preferred among isocyanates compounds are hexamethylene diisocyanate, 2,2,4-trimethylhexane diisocyanate, 2,4,4-trimethylhexamethylene diisocyanate, pentamethylene diisocyanate, m-xylylene diisocyanate, isophorone diisocyanate, bis(isocyanatomethyl)cyclohexane, bis(isocyanatocyclohexyl)methane, 2,5-bis(isocyanatomethyl)bicyclo-[2.2.1]-heptane, 2,6-bis(isocyanatomethyl)bicyclo-[2.2.1]-heptane, tolylene diisocyanate, phenylene diisocyanate, and 4,4'-diphenylmethane diisocyanate, and more preferred are 2,2,4-trimethylhexane diisocyanate, 2,4,4-trimethylhexamethylene diisocyanate, m-xylylene diisocyanate, bis(isocyanatomethyl)cyclohexane, bis(isocyanatocyclohexyl)methane, 2,5-bis(isocyanatomethyl)bicyclo-[2.2.1]-heptane, and 2,6-bis(isocyanatomethyl)bicyclo-[2.2.1]-heptane.

One iso(thio)cyanate compound may be used singly, and two or more iso(thio)cyanate compounds may be used.

Examples of the hydroxy acrylate compound having one or more polymerizable groups include 2-hydroxyethyl acrylate, 2-hydroxypropyl acrylate, 2-hydroxybutyl acrylate, 2-hydroxy-3-phenoxypropyl acrylate, 4-hydroxybutyl acrylate, and 1,4-cyclohexanedimethanol monoacrylate.

(Meth)acrylate (B2) in the present invention is obtained by reacting the thiol compound, the iso(thio)cyanate compound, and the hydroxy (meth)acrylate compound as described above, and the reaction may be performed by using a known method or a method according to a known method.

If at least one (meth)acrylate selected from the group consisting of (meth)acrylate (B1) and (meth)acrylate (B2) is contained as (meth)acrylate (B), the content of (meth)acrylates (B1) and (B2) is not limited to particular values, but preferably 1 to 50% by mass and more preferably 15 to 24% by mass to the total mass of the polymerizable composition for a dental material. If (meth)acrylate (B) is (meth)acrylate (B3-5) described later, it is preferable that the content of (meth)acrylate (B3-5) be also in the above range. In particular, if a component other than allyl compound (A) and (meth)acrylate compound (B), such as a filler and a polymerization initiator described later, is contained, the above range is preferred.

[Polymerizable Compound (B3)]

In addition to one (meth)acrylate selected from the group consisting of (meth)acrylates (B1) and (B2) described above, or in place of the (meth)acrylate, the polymerizable composition of the present invention for a dental material may contain polymerizable compound (B3) (except (meth)acrylates (B1) and (B2)) including at least one polymerizable group selected from a methacryloyl group and an acryloyl group.

The number of polymerizable groups (at least one polymerizable group selected from a methacryloyl group and an acryloyl group) included in polymerizable compound (B3) may be one or two or more. The number of polymerizable groups is preferably 2 or more and 10 or less, more preferably two or more and six or less, and even more preferably two or more and four or less.

Examples of polymerizable compound (B3) including only one polymerizable group include (meth)acrylate (B3-3) including one (meth)acryloyloxy group. Examples of (meth)acrylate (B3-3) include methyl methacrylate, ethyl methacrylate, propyl methacrylate, butyl methacrylate, hexyl methacrylate, cyclohexyl methacrylate, ethoxydiethylene glycol methacrylate, methoxytriethylene glycol methacrylate, phenoxyethyl methacrylate, 2-hydroxyethyl methacrylate, 2-hydroxypropyl methacrylate, 2-hydroxybutyl methacrylate, 2-hydroxy-3-phenoxypropyl methacrylate, 4-hydroxybutyl methacrylate, and 1,4-cyclohexanedimethanol monomethacrylate.

Examples of polymerizable compound (B3) including two or more polymerizable groups include (meth)acrylate (B3-4) include two (meth)acryloyloxy groups. However, (meth)acrylates (B1) and (B2) are not included in the scope of (meth)acrylate (B3-4). Examples of (meth)acrylate (B3-4) include (meth)acrylate having a divalent oxyalkylene group, (meth)acrylate (B3-5) having a urethane bond (except (meth)acrylates (B1) and (B2)), and (meth)acrylate (B3-6) having a cyclic structure.

Examples of the (meth)acrylate having a divalent oxyalkylene group include ethylene glycol dimethacrylate, diethylene glycol dimethacrylate, triethylene glycol dimethacrylate, tetraethylene glycol dimethacrylate, polyethylene glycol dimethacrylate, tripropylene glycol dimethacrylate, tetrapropylene glycol dimethacrylate, and polypropylene glycol dimethacrylate.

Examples of (meth)acrylate (B3-5) having a urethane bond (except (meth)acrylates (B1) and (B2)) include urethane methacrylate as a reaction product of hydroxy methacrylate, such as 2-hydroxyethyl methacrylate, 2-hydroxypropyl methacrylate, 2-hydroxybutyl methacrylate, 2-hydroxy-3-phenoxypropyl methacrylate, 4-hydroxybutyl methacrylate, and 1,4-cyclohexanedimethanol monomethacrylate, and diisocyanate, such as 2,4- or 2,6-toluene diisocyanate, 4,4'-, 2,4'-, or 2,2'-diphenylmethane-diisocyanate, 1,6-hexamethylene diisocyanate, and 2,2,4- or 2,4,4-trimethyl-1,6-hexamethylene-diisocyanate, and examples of such urethane methacrylate include 2,2,4-trimethylhexamethylenebis(2-carbamoyloxyethyl) dimethacrylate (UDMA).

As (meth)acrylate (B3-6) having a cyclic structure, (meth)acrylate having an aromatic structure is preferred, and examples thereof include 2,2-bis[4-(3-methacryloyloxy-2-hydroxypropoxy)phenyl]propane (Bis-GMA), ethylene oxide-modified bisphenol A dimethacrylate, and propylene oxide-modified bisphenol A dimethacrylate.

In using the polymerizable composition of the present invention for a dental material, for example, for a dental adhesive, it is preferable that a polymerizable compound that exhibits an adhesive function be contained as polymerizable compound (B3). Examples of such polymerizable compound (B3) that exhibits an adhesive function include polymerizable compounds having at least one polymerizable group selected from a methacryloyl group and an acryloyl group and an acidic group. Examples of the acidic group include a phosphate residue, a pyrophosphate residue, a thiophosphate residue, a carboxylate residue, and a sulfonate residue.

The polymerizable composition of the present invention for a dental material may contain a polymerizable compound having an acidic group that is not classified into polymerizable compound (B3). Examples of such polymerizable compounds having an acidic group include polymerizable compounds with a sulfonate residue such as styrenesulfonic acid. One of these polymerizable compounds having an acidic group may be used singly, and two or more of them may be used in combination.

If a polymerizable compound having an acidic group described above is contained in the polymerizable composition of the present invention for a dental material, the blend ratio of the polymerizable compound having an acidic group is not limited to particular values, but the polymerizable compound having an acidic group is contained in the polymerizable composition for a dental material in such a manner that the number of polymerizable groups included in the polymerizable compound having an acidic group accounts for, in typical cases, 50% or less of the total number of polymerizable groups in the polymerizable composition for a dental material.

The amount of polymerizable compound (B3) is typically 0 to 60% by weight and preferably 10 to 40% by weight to that of the polymerizable composition of the present invention for a dental material as 100% by weight. In particular, if a component other than allyl compound (A) and (meth) acrylate compound (B), such as a filler and a polymerization initiator described later, is contained, the above range is preferred.

The polymerizable composition of the present invention for a dental material may be composed only of monomer components of allyl compound (A) and (meth)acrylate compound (B), or composed of them together with a component other than the monomer components (such as a filler and a polymerization initiator described later).

In the case of a configuration composed only of the monomer components, the content of allyl compound (A) and (meth)acrylate compound (B) is preferably 90% by mass or more to the total of the composition, and a configuration composed only of allyl compound (A) and (meth) acrylate compound (B) may be employed.

If the polymerizable composition of the present invention for a dental material is composed only of the monomer components, this polymerizable composition for a dental material is occasionally referred to as "the monomer composition for a dental material", and the polymerizable composition of the present invention for a dental material in the case that the polymerizable composition contains the monomer components and a component other than the monomer components (such as a filler and a polymerization initiator) is occasionally referred to as "the composition for a dental material".

The viscosity of the polymerizable composition of the present invention for a dental material is not limited to particular values, but the viscosity at 65° C. is preferable in the range of 1 to 300,000 mPa·s, more preferably in the range of 1 to 100,000 mPa·s, even more preferably in the range of 5 to 60,000 mPa·s, furthermore preferably in the range of 10 to 30,000 mPa·s, and even furthermore preferably in the range of 100 to 10,000 mPa·s. In particular, if the polymerizable composition of the present invention for a dental material contains a filler or a polymerization initiator, it is preferable that the viscosity of the composition be in the above range. At a viscosity higher than the above upper limit value, poor dispersibility is provided when a component such as a filler is added to the polymerizable composition for a dental material, and the poor dispersibility is likely to lead to difficulty in homogeneous mixing. At a viscosity lower than the above lower limit value, on the other hand, more bubbles are incorporated when a component such as a filler is added to the polymerizable composition for a dental material, and these bubbles are likely to cause difficulty in homogeneous mixing, similarly. The polymerizable composition for a dental material undergoes in some cases oligomerization of a part of the monomer components contained therein through storage at high temperature. The above-described viscosity is that of the polymerizable composition for a dental material immediately after preparation before the occurrence of oligomerization.

The hue of the polymerizable composition for a dental material in the present invention is not limited to particular values, but it is preferable that the hue be good because the polymerizable composition is used as a raw material of dental materials. Specifically, the hue represented as APHA is preferably 500 or lower, more preferably 200 or lower, and even more preferably 100 or lower.

In producing the polymerizable composition of the present invention for a dental material, the manner of mixing allyl compound (A) or an oligomer thereof, (meth)acrylate compound (B), and so on is not limited to particular methods. For example, the polymerizable composition of the present invention for a dental material can be obtained by stirring allyl compound (A) or an oligomer thereof, (meth) acrylate compound (B), and so on, which are contained in a container, with warming as appropriate until a homogenous state is reached.

The polymerizable composition of the present invention for a dental material may contain a polymerization inhibitor to enhance the storage stability.

The polymerizable composition of the present invention for a dental material is provided with room-temperature polymerizability, thermal polymerizability, and photopolymerizability by addition of a polymerization initiator described later. Molded bodies obtained by curing the polymerizable composition of the present invention for a dental material have higher mechanical properties than molded bodies obtained by curing any of conventional monomer compositions for a dental material or compositions for a dental material, and especially have both high rupture strength and high breaking energy in a well-balanced manner. In other words, such a molded body is a material having toughness and rigidity in combination.

The polymerizable composition of the present invention for a dental material may contain an additive such as a microbicide, a disinfectant, a stabilizer, and a preservative, as necessary, unless the advantageous effects of the present invention are impaired by the additive.

The polymerizable composition of the present invention for a dental material is preferred for production of dental materials, and the above-described configuration including allyl compound (A) or an oligomer of allyl compound (A), (meth)acrylate compound (B), a polymerization initiator, and a filler is a preferred mode. Such a polymerizable composition for a dental material has room-temperature polymerizability, thermal polymerizability, or photopolymerizability, and can be preferably used, for example, as dental restorative materials. The present inventors found that cured products with high degree of polymerization and superior mechanical strength can be obtained through photopolymerization, even though a compound with allyl compound (A) is used. From this viewpoint, use of a photopolymerization initiator is preferred.

The total blend ratio of allyl compound (A) or an oligomer of allyl compound (A), (meth)acrylate compound (B), and other polymerizable compounds contained as necessary is not limited to particular values, and if a component other than the monomer components such as a filer and a polymerization initiator described later is contained, the total blend ratio may be typically 20 to 80% by weight and preferably in the range of 20 to 50% by weight to the weight of the polymerizable composition for a dental material as 100% by weight.

Common polymerization initiators used in the field of dentistry may be used for the polymerization initiator, and selection is made typically with considering the polymerizability of the polymerizable compound contained in the polymerizable composition for a dental material and polymerization conditions.

In performing room-temperature polymerization, redox-system polymerization initiators as combinations of an oxidant and a reductant are preferred. In using a redox-system polymerization initiator, the oxidant and the reductant are needed to be in the form of separately packaged products and it is required to mix the two immediately before use.

Examples of the oxidant include, but are not limited to, organic peroxides such as diacyl peroxides, peroxy esters, dialkyl peroxides, peroxy ketals, ketone peroxides, and hydroperoxides.

The reductant is not limited to a particular reductant, and tertiary amines are typically used.

In addition to those organic peroxide/amine systems, redox-system polymerization initiators such as a cumene hydroperoxide/thiourea system, an ascorbic acid/Cu$^{2+}$ salt system, and an organic peroxide/amine/sulfinic acid (or a salt thereof) system may be used. Further, tributylborane, organic sulfinic acid, and so on may be used as the polymerization initiator.

In performing thermal polymerization by heating, use of a peroxide or an azo compound is preferred.

Examples of the peroxide include, but are not limited to, benzoyl peroxide, t-butyl hydroperoxide, and cumene hydroperoxide. Examples of the azo compound include, but are not limited to, azobisisobutyronitrile.

In performing photopolymerization by irradiation with a visible ray, redox-system initiators such as α-diketone/tertiary amine, α-diketone/aldehyde, and α-diketone/mercaptan are preferred.

Examples of the photopolymerization initiator include, but are not limited to, α-diketone/reductant, ketal/reductant, and thioxanthone/reductant. Examples of α-diketone include camphorquinone, benzil, and 2,3-pentanedione. Examples of ketal include benzyl dimethyl ketal and benzyl diethyl ketal. Examples of thioxanthone include 2-chlorothioxanthone and 2,4-diethylthioxanthone. Examples of the reductant can include Michler's ketone or the like; tertiary amines such as 2-(dimethylamino)ethyl methacrylate, N,N-bis[(meth)acryloyloxyethyl]-N-methylamine, ethyl N,N-dimethylaminobenzoate, butyl 4-dimethylaminobenzoate, butoxyethyl 4-dimethylaminobenzoate, N-methyldiethanolamine, 4-dimethylaminobenzophenone, N,N-bis(2-hydroxyethyl)-p-toluidine, and dimethylaminophenanthol; aldehydes such as citronellal, laurylaldehyde, phthaldialdehyde, dimethylaminobenzaldehyde, and terephthalaldehyde; and compounds with a thiol group such as 2-mercaptobenzoxazole, decanethiol, 3-mercaptopropyltrimethoxysilane, 4-mercaptoacetophenone, thiosalicylic acid, and thiobenzoic acid. Systems of α-diketone/organic peroxide/reductant obtained by adding an organic peroxide to any of those redox systems are also preferably used.

In performing photopolymerization by irradiation with an ultraviolet ray, benzoin alkyl ether, benzyl dimethyl ketal, and so on are preferred. In addition, (bis)acylphosphine oxides are preferably used as the photopolymerization initiator.

Examples of acylphosphine oxides among (bis)acylphosphine oxides include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, and benzoyl di-(2,6-dimethylphenyl)phosphonate. Examples of bisacylphosphine oxides include bis-(2,6-dichlorobenzoyl) phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis-(2,6-dimethoxybenzoyl) phenylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide, and (2,5,6-trimethylbenzoyl)-2,4,4-trimethylpentylphosphine oxide. Those photopolymerization initiators of (bis)acylphosphine oxides may be used singly, or in combination with any of various reductants such as amines, aldehydes, mercaptans, and sulfinates. Those photopolymerization initiators can be preferably used in combination with any of the above photopolymerization initiators for visible rays.

One of the above polymerization initiators may be used singly, and two or more of them may be mixed for use. The blend ratio of the polymerization initiator is typically 0.01 to 20% by weight and preferably in the range of 0.1 to 5% by weight to the total amount of the polymerizable compounds (allyl compound (A) or an oligomer of allyl compound (A), (meth)acrylate compound (B), and other polymerizable compounds contained as necessary) contained in the polymerizable composition for a dental material as 100% by weight.

Common fillers used in the field of dentistry may be used for the filler. Fillers are roughly classified into organic fillers and inorganic fillers.

Examples of organic fillers include micropowders of polymethyl methacrylate, polyethyl methacrylate, methyl methacrylate-ethyl methacrylate copolymer, crosslinked polymethyl methacrylate, crosslinked polyethyl methacrylate, ethylene-vinyl acetate copolymer, and styrene-butadiene copolymer.

Examples of inorganic fillers include micropowders of glass substances (containing silicon dioxide as a primary component, and oxides of heavy metal, boron, aluminum, and so on, as necessary), ceramics, diatomaceous earth, kaolin, clay minerals (e.g., montmorillonite), activated clay, synthesized zeolites, micas, calcium fluoride, ytterbium fluoride, calcium phosphate, barium sulfate, zirconium dioxide, titanium dioxide, and hydroxyapatite. Specific examples of such inorganic fillers include barium borosilicate glass (such as Kimble RAYSORB T3000, Schott 8235, Schott GM27884, and Schott GM39923), strontium boroaluminosilicate glass (such as RAYSORB T4000, Schott G018-093, and Schott GM32087), lanthanum glass (such as Schott GM31684), fluoroaluminosilicate glass (such as Schott G018-091 and Schott G018-117), and zirconium and/or cesium-containing boroaluminosilicate glass (such as Schott G018-307, G018-308, and G018-310).

It is allowable to use an organic/inorganic composite filler obtained in such a manner that a polymerizable compound is added in advance to any of those inorganic fillers to form a paste, and the paste is then cured through polymerization and the cured product is pulverized.

A composition obtained by blending a microfiller of 0.1 µm or smaller in particle size with the polymerizable composition for a dental material is a preferred mode for dental composite resin. The material of such a filler of small particle size is preferably silica (e.g., product name: AELOSIL), alumina, zirconia, titania, or the like. Blending such an inorganic filler of small particle size is advantageous to impart smoothness after polishing to molded bodies obtained by curing composite resin.

Those fillers are occasionally surface-treated with a silane coupling agent or the like according to the purpose. Used for the surface-treating agent are known silane coupling agents such as organic silicon compounds including γ-methacryloxyalkyltrimethoxysilane (the number of carbon atoms between a methacryloxy group and a silicon atom: 3 to 12), γ-methacryloxyalkyltriethoxysilane (the number of carbon atoms between a methacryloxy group and a silicon atom: 3 to 12), vinyltrimethoxysilane, vinylethoxysilane, and vinyltriacetoxysilane.

One of those fillers may be used singly, and two or more of them may be mixed for use. The blend ratio of the filler may be appropriately determined with considering operability (consistency) of the polymerizable composition for a dental material (e.g., as composite resin paste) and the mechanical properties of a molded body obtained by curing the polymerizable composition, and the blend ratio is typically 10 to 2000 parts by weight, preferably 50 to 1000 parts by weight, and more preferably 100 to 600 parts by weight to the weight of all of the components contained in the polymerizable composition for a dental material other than the filler as 100 parts by weight.

According to the purpose, the polymerizable composition of the present invention for a dental material may appropriately contain a component other than allyl compound (A) or an oligomer of allyl compound (A), (meth)acrylate compound (B), other polymerizable compounds contained as necessary, the above-described polymerization initiator, and the above-described filler in the present invention. For example, the polymerizable composition of the present invention for a dental material may contain the above-described polymerization inhibitor to enhance the storage stability. Further, the polymerizable composition of the present invention for a dental material may contain a known coloring substance such as a pigment and a dye to adjust the color tone. Furthermore, the polymerizable composition of the present invention for a dental material may contain a known reinforcing material such as a fiber to impart enhanced strength to a molded body obtained by curing.

The polymerizable composition of the present invention for a dental material can be cured under conditions suitable for the polymerization process of the above-described polymerization initiator. In the case that the polymerizable composition of the present invention for a dental material contains a photopolymerization initiator for visible light irradiation, for example, a desired cured molded body can be obtained in such manner that the polymerizable composition for a dental material is processed into a predetermined shape, and then irradiated with visible light by using a known light irradiator for a predetermined time. The conditions including irradiation intensity and irradiation intensity may be appropriately changed according to the curability of the polymerizable composition for a dental material. A molded body cured through light irradiation such as visible light irradiation may be further provided with enhanced mechanical properties of a molded body by heat treatment under suitable conditions.

Molded bodies obtained by curing the polymerizable composition of the present invention for a dental material in the described manner can be preferably used as dental materials.

Use of the polymerizable composition of the present invention for a dental material is not limited to particular fashions, and the polymerizable composition of the present invention for a dental material may be used for any commonly known method of using dental materials. In using the polymerizable composition of the present invention for a dental material as composite resin for filling caries cavities, for example, a dental cavity in the oral cavity is filled with the polymerizable composition for a dental material, which is then photo-cured by using a known light irradiator, by which the purpose is successfully achieved. In using as composite resin for tooth crowns, the polymerizable composition for a dental material is processed into an appropriate shape, then photo-cured by using a known light irradiator, and further heat-treated under predetermined conditions, by which a desired tooth crown material is successfully obtained.

The polymerizable composition of the present invention for a dental material is preferred for a dental material, and examples of dental materials include dental restorative materials, resins for denture bases, lining materials for denture bases, impression materials, materials for coalescence (resin cements and resin-modified glass ionomer cements), dental adhesive materials (adhesive materials for tooth movement and adhesive materials for application to dental cavities), dental fissure sealants, resin blocks for CAD/CAM, temporary crowns, and materials for artificial teeth.

Moreover, the polymerizable composition of the present invention for a dental material can be preferably used as a dental restorative material (e.g., dental composite resin). Dental restorative materials are classified by scope of application into composite resin for molar teeth, composite resin for tooth crowns, composite resin for filling caries cavities, composite resin for abutment construction, composite resin for filling restoration, and so on, and molded bodies obtained by curing the polymerizable composition of the present invention for a dental material can be particularly preferably used as composite resin for molar teeth because of their high mechanical properties.

EXAMPLES

Hereinafter, the present invention will be more specifically described with reference to Examples; however, the present invention is not limited to Examples in the following.

[Production Example] Synthesis of Thiourethane Acrylate (B-a1)

Abbreviations for compounds used in Production Example of the present invention are listed in the following.
HPA: 2-hydroxypropyl acrylate
XDI: m-xylylene diisocyanate
THIOL: mixture of 5,7-dimercaptomethyl-1,11-dimercapto-3,6,9-trithiaundecane, 4,7-dimercaptomethyl-1,11-dimercapto-3,6,9-trithiaundecane, and 4,8-dimercaptomethyl-1,11-dimercapto-3,6,9-trithiaundecane
DBTDL: dibutyltin dilaurate
BHT: dibutylhydroxytoluene A sufficiently dried 100-mL four-neck flask equipped with a stirring blade and a thermometer was charged with 0.1 parts by weight of DBTDL, 0.05 parts by weight of BHT, 21.35 parts by weight of XDI, and 2.09 parts by weight of THIOL, and the mixture was dissolved to form a homogenous solution, which was then reacted at 80° C. for 4 hours to afford a solution containing an intermediate. The temperature of this solution was raised to 90° C., and 26.56 parts by weight of HPA was further added dropwise to the solution over 1 hour. Because the inner temperature increased by the heat of reaction during dropwise addition, the rate of dropwise addition was controlled to keep the temperature at 90° C. or lower. After the whole of the solution was added dropwise, the resultant was reacted for 10 hours with the reaction temperature retained at 90° C. During the reaction, the progression of the reaction was traced through HPLC analysis to confirm the end point of the reaction. The product was discharged from the reactor to afford 50 g of thiourethane acrylate (B-a1) (acrylate (B-a1)). The viscosity at 65° C. was 1790 mPa·s. The refractive index at 25° C. was 1.5271. FIG. 1 shows the IR spectrum of thiourethane acrylate (B-a1).

Abbreviations for compounds used in Examples of the present invention are listed in the following.

DAP: diallyl phthalate
BAC: diethylene glycol bisallyl carbonate
DAC: diallyl carbonate
DVB: divinylbenzene
CQ: camphorquinone
DMAB2-BE: 2-butoxyethyl 4-(dimethylamino)benzoate
DAPCH: 1,1-di(t-amylperoxy)cyclohexane

[Method for Producing Test Pieces for Bend Test—Part 1]

Shown in the following is a method for producing test pieces for bend test when a test subject was produced through photopolymerization in Examples and Comparative Examples of the present invention.

(Production of Test Pieces for Bend Test with Photopolymerization Method)

To 30 parts by weight of a monomer composition obtained in each of Examples and Comparative Examples, 0.09 parts by weight of CQ and 0.09 parts by weight of DMAB2-BE were added, and the resultant was stirred at room temperature until a homogenous state was reached. Therewith, 70 parts by weight of silica glass (Fuselex-X (TATSUMORI LTD.)) was further blended, and the mixture was stirred with a mortar until a homogenous state was reached, and the resultant was degassed to prepare a composition for a dental material. The resulting composition for a dental material was put in a stainless-steel mold of 2×2×25 mm, and irradiated with light by using a visible light irradiator (Solidilite V produced by SHOFU INC.) for 3 minutes for each face, for 6 minutes in total. The test piece was removed from the mold, and further heat-treated in an oven at 130° C. for 2 hours. The test piece was taken out of the oven, cooled to room temperature, and then soaked in distilled water in a sealable sample bottle and retained at 37° C. for 24 hours. The resultant was used as a test piece (a test piece for bend test obtained with a photopolymerization method).

[Method for Producing Test Pieces for Bend Test—Part 2]

Shown in the following is a method for producing test pieces for bend test when a test subject was produced through thermal polymerization in Examples and Comparative Examples of the present invention.

(Production of Test Pieces for Bend Test with Thermal Polymerization Method—Part 1)

To 30 parts by weight of a monomer composition obtained in each of Examples and Comparative Examples, 0.24 parts by weight of DAPCH was added, and the resultant was stirred at room temperature until a homogenous state was reached. Therewith, 70 parts by weight of silica glass (Fuselex-X (TATSUMORI LTD.)) was further blended, and the mixture was stirred with a mortar until a homogenous state was reached, and the resultant was degassed to prepare a composition for a dental material. The resulting composition for a dental material was put in a glass mold of 30 mm in diameter and 50 mm in height, and thermal polymerization was performed by retaining the composition in an oven with a maximum temperature of 120° C. for 48 hours in total. The resulting thermally-polymerized molded body was heat-treated in an oven at 130° C. for 2 hours. The molded body was taken out of the oven, cooled to room temperature, and then cut into a test piece of 2×2×25 m in size. The test piece obtained was soaked in distilled water in a sealable sample bottle and retained at 37° C. for 24 hours. The resultant was used as a test piece (test piece 1 for bend test obtained with a thermal polymerization method).

[Method for Producing Test Pieces for Bend Test—Part 3]

Shown in the following is a method for producing test pieces for bend test when a test subject was produced through thermal polymerization and then soaked in distilled water for a week in Examples and Comparative Example of the present invention.

(Production of Test Pieces for Bend Test with Thermal Polymerization Method—Part 2)

To 30 parts by weight of a monomer composition obtained in each of Examples and Comparative Examples, 0.24 parts by weight of DAPCH was added, and the resultant was stirred at room temperature until a homogenous state was reached. Therewith, 70 parts by weight of silica glass (Fuselex-X (TATSUMORI LTD.)) was further blended, and the mixture was stirred with a mortar until a homogenous state was reached, and the resultant was degassed to prepare a composition for a dental material. The resulting composition for a dental material was put in a glass mold of 30 mm in diameter and 50 mm in height, and thermal polymerization was performed by retaining the composition in an oven with a maximum temperature of 120° C. for 48 hours in total. The resulting thermally-polymerized molded body was heat-treated in an oven at 130° C. for 2 hours. The molded body was taken out of the oven, cooled to room temperature, and then cut into a test piece of 2×2×25 m in size. The test piece obtained was soaked in distilled water in a sealable sample bottle and retained at 37° C. for a week. The resultant was used as a test piece (test piece 2 for bend test obtained with a thermal polymerization method).

(Bend Test)

Each test piece produced with any of the above methods was subjected to three-point bend test by using a universal tester (tester model 210X produced by INTESCO co., ltd.) with the distance between fulcrums set to 20 mm at a crosshead speed of 1 mm/min.

Example 1

Put in a container were 80 parts by weight of thiourethane acrylate (B-a1) obtained in Production Example and 20 parts by weight of DAP, and the resultant was stirred at 50° C. until a homogenous state was reached to afford monomer composition (1) for a dental material. From monomer composition (1) for a dental material obtained, composition (1-1) for a dental material and a test piece (a test piece for bend test obtained with a photopolymerization method) were obtained in accordance with the methods described in the sections (Production of Test Pieces for Bend Test with Photopolymerization Method) and (Bend Test), and the test piece was subjected to bend test. The flexural strength and breaking energy were found to be 214 MPa and 24 mJ, respectively.

The result is shown in Table 1.

Example 2

Put in a container were 70 parts by weight of thiourethane acrylate (B-a1) obtained in Production Example and 30 parts by weight of DAP, and the resultant was stirred at 50° C. until a homogenous state was reached to afford monomer composition (2) for a dental material. From monomer composition (2) for a dental material obtained, composition (2-1) for a dental material and a test piece (a test piece for bend test obtained with a photopolymerization method) were obtained in accordance with the methods described in the sections (Production of Test Pieces for Bend Test with Photopolymerization Method) and (Bend Test), and the test piece was subjected to bend test. The flexural strength and breaking energy were found to be 202 MPa and 28 mJ, respectively. The result is shown in Table 1.

Example 3

Put in a container were 60 parts by weight of thiourethane acrylate (B-a1) obtained in Production Example and 40 parts by weight of DAP, and the resultant was stirred at 50° C. until a homogenous state was reached to afford monomer composition (3) for a dental material. From monomer composition (3) for a dental material obtained, composition (3-1) for a dental material and a test piece (a test piece for bend test obtained with a photopolymerization method) were obtained in accordance with the methods described in the sections (Production of Test Pieces for Bend Test with Photopolymerization Method) and (Bend Test), and the test piece was subjected to bend test. The flexural strength and breaking energy were found to be 182 MPa and 23 mJ, respectively. The result is shown in Table 1.

Example 4

Put in a container were 80 parts by weight of thiourethane acrylate (B-a1) obtained in Production Example and 20 parts by weight of BAC, and the resultant was stirred at 50° C. until a homogenous state was reached to afford monomer composition (4) for a dental material. From monomer composition (4) for a dental material obtained, composition (4-1) for a dental material and a test piece (a test piece for bend test obtained with a photopolymerization method) were obtained in accordance with the methods described in the sections (Production of Test Pieces for Bend Test with Photopolymerization Method) and (Bend Test), and the test piece was subjected to bend test. The flexural strength and breaking energy were found to be 209 MPa and 26 mJ, respectively. The result is shown in Table 1.

Example 5

Put in a container were 70 parts by weight of thiourethane acrylate (B-a1) obtained in Production Example and 30 parts by weight of BAC, and the resultant was stirred at 50° C. until a homogenous state was reached to afford monomer composition (5) for a dental material. From monomer composition (5) for a dental material obtained, composition (5-1) for a dental material and a test piece (a test piece for bend test obtained with a photopolymerization method) were obtained in accordance with the methods described in the sections (Production of Test Pieces for Bend Test with Photopolymerization Method) and (Bend Test), and the test piece was subjected to bend test. The flexural strength and breaking energy were found to be 195 MPa and 30 mJ, respectively. The result is shown in Table 1.

Example 6

Put in a container were 60 parts by weight of thiourethane acrylate (B-a1) obtained in Production Example and 40 parts by weight of BAC, and the resultant was stirred at 50° C. until a homogenous state was reached to afford monomer composition (6) for a dental material. From monomer composition (6) for a dental material obtained, composition (6-1) for a dental material and a test piece (a test piece for bend test obtained with a photopolymerization method) were obtained in accordance with the methods described in the sections (Production of Test Pieces for Bend Test with Photopolymerization Method) and (Bend Test), and the test piece was subjected to bend test. The flexural strength and breaking energy were found to be 177 MPa and 24 mJ, respectively. The result is shown in Table 1.

Comparative Example 1

Put in a container were 80 parts by weight of thiourethane acrylate (B-a1) obtained in Production Example and 20 parts by weight of DVB, and the resultant was stirred at 50° C. until a homogenous state was reached to afford monomer composition (7) for a dental material. From monomer composition (7) for a dental material obtained, composition (7-1) for a dental material and a test piece (a test piece for bend test obtained with a photopolymerization method) were obtained in accordance with the methods described in the sections (Production of Test Pieces for Bend Test with Photopolymerization Method) and (Bend Test), and the test piece was subjected to bend test. The flexural strength and breaking energy were found to be 168 MPa and 19 mJ, respectively. The result is shown in Table 1.

TABLE 1

| Photopoly-merization | | Feed ratio | | | Mechanical properties | |
| --- | --- | --- | --- | --- | --- | --- |
| | Main mono-mer | Weight ratio [%] | Diluting mono-mer | Weight ratio [%] | Flexural strength [MPa] | Breaking energy [mj] |
| Example 1 | B-a1 | 80 | DAP | 20 | 214 | 24 |
| 2 | B-a1 | 70 | DAP | 30 | 202 | 28 |
| 3 | B-a1 | 60 | DAP | 40 | 182 | 23 |
| 4 | B-a1 | 80 | BAC | 20 | 209 | 26 |
| 5 | B-a1 | 70 | BAC | 30 | 195 | 30 |
| 6 | B-a1 | 60 | BAC | 40 | 177 | 24 |
| Comparative Example 1 | B-a1 | 80 | DVB | 20 | 168 | 19 |

Example 7

Put in a container were 80 parts by weight of thiourethane acrylate (B-a1) obtained in Production Example and 20 parts by weight of DAP, and the resultant was stirred at 50° C. until a homogenous state was reached to afford monomer composition (8) for a dental material. From monomer composition (8) for a dental material obtained, composition (8-1) for a dental material and a test piece (test piece 1 for bend test obtained with a thermal polymerization method) were obtained in accordance with the methods described in the sections (Production of Test Pieces for Bend Test with Thermal Polymerization Method—Part 1) and (Bend Test), and the test piece was subjected to bend test. The flexural strength and breaking energy were found to be 257 MPa and 42 mJ, respectively. The result is shown in Table 2.

Example 8

Put in a container were 70 parts by weight of thiourethane acrylate (B-a1) obtained in Production Example and 30 parts by weight of DAP, and the resultant was stirred at 50° C. until a homogenous state was reached to afford monomer composition (9) for a dental material. From monomer composition (9) for a dental material obtained, composition (9-1) for a dental material and a test piece (test piece 1 for bend test obtained with a thermal polymerization method) were obtained in accordance with the methods described in the sections (Production of Test Pieces for Bend Test with Thermal Polymerization Method—Part 1) and (Bend Test), and the test piece was subjected to bend test. The flexural strength and breaking energy were found to be 232 MPa and 30 mJ, respectively. The result is shown in Table 2.

Example 9

Put in a container were 60 parts by weight of thiourethane acrylate (B-a1) obtained in Production Example and 40 parts by weight of DAP, and the resultant was stirred at 50° C. until a homogenous state was reached to afford monomer composition (10) for a dental material. From monomer composition (10) for a dental material obtained, composition (10-1) for a dental material and a test piece (test piece 1 for bend test obtained with a thermal polymerization method) were obtained in accordance with the methods described in the sections (Production of Test Pieces for Bend Test with Thermal Polymerization Method—Part 1) and (Bend Test), and the test piece was subjected to bend test. The flexural strength and breaking energy were found to be 212 MPa and 25 mJ, respectively. The result is shown in Table 2.

Example 10

Put in a container were 80 parts by weight of thiourethane acrylate (B-a1) obtained in Production Example and 20 parts by weight of BAC, and the resultant was stirred at 50° C. until a homogenous state was reached to afford monomer composition (11) for a dental material. From monomer composition (11) for a dental material obtained, composition (11-1) for a dental material and a test piece (test piece 1 for bend test obtained with a thermal polymerization method) were obtained in accordance with the methods described in the sections (Production of Test Pieces for Bend Test with Thermal Polymerization Method—Part 1) and (Bend Test), and the test piece was subjected to bend test. The flexural strength and breaking energy were found to be 248 MPa and 38 mJ, respectively. The result is shown in Table 2.

Example 11

Put in a container were 70 parts by weight of thiourethane acrylate (B-a1) obtained in Production Example and 30 parts by weight of BAC, and the resultant was stirred at 50° C. until a homogenous state was reached to afford monomer composition (12) for a dental material. From monomer composition (12) for a dental material obtained, composition (12-1) for a dental material and a test piece (test piece 1 for bend test obtained with a thermal polymerization method)
were obtained in accordance with the methods described in the sections (Production of Test Pieces for Bend Test with Thermal Polymerization Method—Part 1) and (Bend Test), and the test piece was subjected to bend test. The flexural strength and breaking energy were found to be 228 MPa and 33 mJ, respectively. The result is shown in Table 2.

Example 12

Put in a container were 60 parts by weight of thiourethane acrylate (B-a1) obtained in Production Example and 40 parts by weight of BAC, and the resultant was stirred at 50° C. until a homogenous state was reached to afford monomer composition (13) for a dental material. From monomer composition (13) for a dental material obtained, composition (13-1) for a dental material and a test piece (test piece 1 for bend test obtained with a thermal polymerization method) were obtained in accordance with the methods described in the sections (Production of Test Pieces for Bend Test with Thermal Polymerization Method—Part 1) and (Bend Test), and the test piece was subjected to bend test. The flexural strength and breaking energy were found to be 206 MPa and 24 mJ, respectively. The result is shown in Table 2.

Comparative Example 2

Put in a container were 80 parts by weight of thiourethane acrylate (B-a1) obtained in Production Example and 20 parts by weight of DVB, and the resultant was stirred at 50° C. until a homogenous state was reached to afford monomer composition (14) for a dental material. From monomer composition (14) for a dental material obtained, composition (14-1) for a dental material and a test piece (test piece 1 for bend test obtained with a thermal polymerization method) were obtained in accordance with the methods described in the sections (Production of Test Pieces for Bend Test with Thermal Polymerization Method—Part 1) and (Bend Test), and the test piece was subjected to bend test. The flexural strength and breaking energy were found to be 195 MPa and 21 mJ, respectively. The result is shown in Table 2.

TABLE 2

| | | Feed ratio | | | Mechanical properties | |
|---|---|---|---|---|---|---|
| Thermal polymeri-zation | Main mono-mer | Weight ratio [%] | Diluting mono-mer | Weight ratio [%] | Flexural strength [MPa] | Breaking energy [mj] |
| Example 7 | B-a1 | 80 | DAP | 20 | 257 | 42 |
| 8 | B-a1 | 70 | DAP | 30 | 232 | 30 |
| 9 | B-a1 | 60 | DAP | 40 | 212 | 25 |
| 10 | B-a1 | 80 | BAC | 20 | 248 | 38 |
| 11 | B-a1 | 70 | BAC | 30 | 228 | 33 |
| 12 | B-a1 | 60 | BAC | 40 | 206 | 24 |
| Comparative Example 2 | B-a1 | 80 | DVB | 20 | 195 | 21 |

It can be understood that molded bodies obtained by curing the polymerizable composition of the present invention for a dental material had enhanced flexural strength and enhanced breaking energy compared with molded bodies obtained by curing a conventional polymerizable composition for a dental material. That is, it was demonstrated that use of a specific compound including an allyl group as a diluting monomer imparts enhanced flexural strength and enhanced toughness to molded bodies obtained by curing a polymerizable composition for a dental material.

[Water Absorbency Test]

Shown in the following is a method of water absorbency test when a test piece was produced through photopolymerization with a washer-shaped mold in Examples 13 and 14 and Comparative Examples 3 and 4 of the present invention described later.

(Production of Test Pieces for Water Absorbency Test)

To 100 parts by weight of a monomer composition obtained in each of Examples and Comparative Examples, 0.5 parts by weight of CQ and 0.5 parts by weight of DMAB2-BE were added, and the resultant was stirred at room temperature until a homogenous state was reached, and further degassed to prepare a composition for a dental material. Subsequently, a template film was placed on a glass sheet, and a washer-shaped mold of 05 mm in inner diameter and 1.0 mm in thickness was placed on the template film. The composition for a dental material prepared was poured into the washer-shaped mold, and the top was covered with a glass sheet and pressed to push out an excessive portion of the composition for a dental material from the mold. The product in which the mold filled with the composition for a dental material was sandwiched by two glass sheets was used as a kit for producing a test piece for water absorbency test. The kit for producing a test piece for water absorbency test was fixed with a clip, and irradiated with light by using a visible light irradiator (Solidilite V produced by SHOFU INC.) for 3 minutes for each face, for 6 minutes in total. The washer-shaped mold was taken out of the kit for producing a test piece for water absorbency test, the photo-cured dental material composition was taken out of the washer-shaped mold, and an excessive portion of the photo-cured dental material composition was removed to afford a cylindrical test piece for water absorbency test. These operations were repeated 5 times to produce five test pieces for water absorbency test. The test pieces produced were stored in a desiccator kept at 37±1° C., 22 hours thereafter the samples were taken out of the desiccator and placed in a desiccator kept at 231° C. for 2 hours, and then weighed with a precision of 0.1 mg. The storage in a desiccator for 24 hours in total and weight measurement after storage were repeated until the mass reduction of each test piece for water absorbency test 24 hours after the initiation of storage reached under 0.1 mg. When a constant mass was reached (in other words, when the mass reduction in 24 hours reached less than 0.1 mg), the mass was determined as m1. After the mass m1 was measured, the thickness and diameter of each test piece for water absorbency test was measured with a micrometer to calculate the volume (v) of the test piece. The test pieces for water absorbency test after being measured for volume were placed in a sample bottle, and distilled water in an amount of 50 mL or more in total was poured into the sample bottle to provide each test piece with 10 mL or more of distilled water, and the sample bottle was stored in a desiccator kept at 37±1° C. for a week. The test pieces for water absorbency test were taken out of distilled water, moisture on the surfaces were wiped out, and each test piece was thoroughly shaken in the air for 15 seconds and weighed 1 minute after being taken out of distilled water. The mass at this time was determined as m2. After weighing for m2, storage for 24 hours and measurement with the same operations as in weighing for m1 were repeated until the mass reduction of each test piece for water absorbency test 24 hours after the initiation of storage reached under 0.1 mg. When a constant mass was reached, the mass was determined as m3. A mass of m2 minus m3 was divided by the volume v of a test piece for water absorbency test when m1 was measured, and the resulting value was defined as the water absorption ($\mu g/mm^3$). The mean value for the five test pieces for water absorbency test was calculated, and employed as the water absorption in each of Examples and Comparative Examples.

Example 13

Put in a container were 80 parts by weight of UDMA and 20 parts by weight of DAP, and the resultant was stirred at 50° C. until a homogenous state was reached to afford monomer composition (15) for a dental material. From monomer composition (15) for a dental material obtained, composition (15-1) for a dental material and a test piece for water absorbency test were obtained in accordance with the method described in the section (Production of Test Pieces for Water Absorbency Test), and the test piece was subjected to water absorbency test. The water absorption was found to be 31.4 $\mu g/mm^3$. The result is shown in Table 3.

Example 14, Comparative Example 3, Comparative Example 4

Monomer compositions (16) to (18) for a dental material according to Example 14, Comparative Example 3, and Comparative Example 4 were obtained under the same conditions as in Example 13, except that the types and feed ratios of the main monomer and diluting monomer were changed as shown in Table 3. From monomer compositions (16) to (18) for a dental material obtained, compositions (16-1) to (18-1) for a dental material and test pieces for water absorbency test were obtained in accordance with the method described in the section (Production of Test Pieces for Water Absorbency Test), and the test pieces were subjected to water absorbency test. The results for Example 14, Comparative Example 3, and Comparative Example 4 are shown in Table 3.

TABLE 3

| Water absorbency test | | Feed ratio | | | Physical property value |
|---|---|---|---|---|---|
| | Main monomer | Weight ratio [%] | Diluting monomer | Weight ratio [%] | Water absorption [$\mu g/mm^3$] |
| Example 13 | UDMA | 80 | DAP | 20 | 31.4 |
| 14 | UDMA | 70 | DAP | 30 | 26.9 |
| Comparative 3 | UDMA | 80 | TEGDMA | 20 | 41.2 |
| Example 4 | UDMA | 70 | TEGDMA | 30 | 44.2 |

It can be understood that molded bodies obtained by curing the polymerizable composition of the present invention for a dental material exhibited reduced water absorption compared with molded bodies obtained by curing a conventional polymerizable composition for a dental material. That is, it was demonstrated that use of a specific compound including an allyl group as a diluting monomer can reduce water absorption in molded bodies obtained by curing a polymerizable composition for a dental material.

Example 15

Put in a container were 80 parts by weight of UDMA and 20 parts by weight of DAP, and the resultant was stirred at 50° C. until a homogenous state was reached to afford monomer composition (19) for a dental material. From monomer composition (19) for a dental material obtained, composition (19-1) for a dental material and test pieces (test piece 1 for bend test obtained with a thermal polymerization method) and (test piece 2 for bend test obtained with a thermal polymerization method) were obtained in accordance with the methods described in the sections (Production of Test Pieces for Bend Test obtained with Thermal Polymerization Method—Part 1), (Production of Test Pieces for Bend Test obtained with Thermal Polymerization Method—Part 2), and (Bend Test), and the test pieces were subjected to bend test. By subtracting the flexural strength of (test piece 2 for bend test obtained with a thermal polymerization method) soaked for a week from the flexural strength of (test piece 1 for bend test obtained with a thermal polymerization method) soaked for a day, lowering of flexural strength due to absorption of water was determined to be 14 MPa. The result is shown in Table 4.

Example 16, Comparative Examples 5, 6

Monomer compositions (20) to (22) for a dental material according to Example 16, Comparative Example 5, and Comparative Example 6 were obtained under the same conditions as in Example 15, except that the types and feed ratios of the main monomer and diluting monomer were changed as shown in Table 3. From monomer compositions (20) to (22) for a dental material obtained, compositions (20-1) to (22-1) for a dental material and test pieces (test piece 1 for bend test obtained with a thermal polymerization method) and (test piece 2 for bend test obtained with a thermal polymerization method) were obtained in accordance with the methods described in the sections (Production of Test Pieces for Bend Test obtained with Thermal Polymerization Method—Part 1), (Production of Test Pieces for Bend Test obtained with Thermal Polymerization Method—Part 2), and (Bend Test), and the test pieces were subjected to bend test. Lowering of flexural strength due to absorption of water was determined by subtracting the flexural strength of (test piece 2 for bend test obtained with a thermal polymerization method) soaked for a week from the flexural strength of (test piece 1 for bend test obtained with a thermal polymerization method) soaked for a day. The results for Example 16, Comparative Example 5, and Comparative Example 6 are shown in Table 4.

It can be understood that molded bodies obtained by curing the polymerizable composition of the present invention for a dental material underwent lowering of strength due to absorption of water to lower degree than molded bodies obtained by curing a conventional polymerizable composition for a dental material. That is, it was demonstrated that use of a compound including an allyl group as a diluting monomer can reduce lowering of strength due to absorption of water in molded bodies obtained by curing a polymerizable composition for a dental material.

[Evaluation of Polymerizability]

Shown in the following is a method of degree of polymerization when a test subject was cured through photopolymerization in Examples and Comparative Examples of the present invention.

(Polymerizability Evaluation Test with Photopolymerization Method)

To 100 parts by weight of a monomer composition obtained in each of Examples and Comparative Examples, 0.3 parts by weight of CQ and 0.3 parts by weight of DMAB2-BE were added, and the resultant was stirred at room temperature until a homogenous state was reached. The composition for a dental material is placed on a sample stage of an FT-IR Spectrometer (Spectrum two produced by PerkinElmer, Inc.), and subjected to FT-IR measurement. The measurement was performed twice for each composition for a dental material: the first measurement was performed without light irradiation; and the second measurement was performed after 20-second light irradiation. In the measurement, a Translux® 2Wave (produced by Kulzer Japan Co., Ltd.) was used for light irradiation.

(Method for Calculating Degree of Polymerization)

With use of absorbance and wavenumber data obtained through the FT-IR measurement in each of Examples and Comparative Examples, degree of polymerization was calculated with the following procedure.

First, an area value for carbonyl groups (1660 to 1800 $cm^{-1}$), which represent carbon-oxygen double bonds in a composition for a dental material, before light irradiation (AreaCOl) was determined as a reference spectrum, and an area value for carbonyl groups of the composition for a dental material after 20-second light irradiation (AreaCOs) was acquired in the same manner. Subsequently, a spectrum area value for carbon-carbon double bonds (1610 to 1660 $cm^{-1}$) of the composition for a dental material before light irradiation (AreaCCl) was determined, and an area value for carbon-carbon double bonds of the composition for a dental material after 20-second light irradiation (AreaCCs) was acquired in the same manner. On the basis of the area values

TABLE 4

| | | Feed ratio | | | Mechanical properties | |
|---|---|---|---|---|---|---|
| Variation of flexural strength due to absorption of water | Main monomer | Weight ratio [%] | Diluting monomer | Weight ratio [%] | Lowering of flexural strength [MPa] | Viscosity [mPa·s] |
| Example 15 | UDMA | 80 | DAP | 20 | 14 | 1010 |
| 16 | B-a1 | 80 | DAP | 20 | 9 | 11700 |
| Comparative 5 | UDMA | 80 | TEGDMA | 20 | 26 | 2500 |
| Example 6 | B-a1 | 80 | TEGDMA | 20 | 21 | 12400 | acquired, the conversion rate of carbon-carbon double bonds was calculated by using [Calculation Formula 1] in the following.

$$[\text{Calculation Formula 1}] \quad \left(1 - \frac{\frac{AreaCCs}{AreaCOs}}{\frac{AreaCC1}{AreaCO1}}\right) \times 100 \quad [\text{Math. 1}]$$

Example 17

Put in a container were 80 parts by weight of thiourethane acrylate (B-a1) obtained in Production Example and 20 parts by weight of DAP, and the resultant was stirred at 50° C. until a homogenous state was reached to afford monomer composition (23) for a dental material. From monomer composition (23) for a dental material obtained, composition (23-1) for a dental material was obtained in accordance with the methods described in the sections (Polymerizability Evaluation Test with Photopolymerization Method) and (Method for Calculating Degree of Polymerization), and the degree of polymerization was calculated to find a conversion rate of 81%. The result is shown in Table 5.

Examples 18, 19, Comparative Examples 7, 8

Monomer compositions (24) to (27) for a dental material according to Examples 18 and 19 and Comparative Examples 7 and 8 were obtained under the same conditions as in Example 17, except that the types and feed ratios of the main monomer and diluting monomer were changed as shown in Table 5. From monomer compositions (24) to (27) for a dental material obtained, compositions (24-1) to (27-1) for a dental material were obtained in accordance with the methods described in the sections (Polymerizability Evaluation Test with Photopolymerization Method) and (Method for Calculating Degree of Polymerization), and the degrees of polymerization were calculated. The results for Examples 18 and 19 and Comparative Examples 7 and 8 are shown in Table 5.

TABLE 5

| Evaluation of degree of poly-merization | | Feed ratio | | | Degree of polymerization Conversion rate [%] |
|---|---|---|---|---|---|
| | | Main monomer | Weight ratio [%] | Diluting monomer | Weight ratio [%] | |
| Example | 17 | B-a1 | 80 | DAP | 20 | 81 |
| | 18 | B-a1 | 80 | BAC | 20 | 93 |
| | 19 | B-a1 | 80 | DAC | 20 | 94 |
| Comparative Example | 7 | B-a1 | 80 | DVB | 20 | 44 |
| | 8 | B-a1 | 80 | TEGDMA | 20 | 72 |

Example 20

Put in a container were 80 parts by weight of UDMA and 20 parts by weight of DAP, and the resultant was stirred at 50° C. until a homogenous state was reached to afford monomer composition (28) for a dental material. From monomer composition (28) for a dental material obtained, composition (28-1) for a dental material was obtained in accordance with the methods described in the sections (Polymerizability Evaluation Test with Photopolymerization Method) and (Method for Calculating Degree of Polymerization), and the degree of polymerization was calculated to find a conversion rate of 85%. The result is shown in Table 6.

Examples 21 to 28, Comparative Examples 9 to 12

Monomer compositions (29) to (40) for a dental material according to Examples 21 to 28 and Comparative Examples 9 to 12 were obtained under the same conditions as in Example 20, except that the types and feed ratios of the main monomer and diluting monomer were changed as shown in Table 6. From monomer compositions (29) to (40) for a dental material obtained, compositions (29-1) to (40-1) for a dental material were obtained in accordance with the methods described in the sections (Polymerizability Evaluation Test with Photopolymerization Method) and (Method for Calculating Degree of Polymerization), and the degrees of polymerization were calculated. The results for Examples 20 to 28 and Comparative Examples 9 to 12 are shown in Table 6.

TABLE 6

| Evaluation of degree of polymerization | | Feed ratio | | | | Degree of polymeri-zation Conversion rate [%] |
|---|---|---|---|---|---|---|
| | | Main monomer | Weight ratio [%] | Diluting monomer | Weight ratio [%] | |
| Example | 20 | UDMA | 80 | DAP | 20 | 85 |
| | 21 | UDMA | 70 | DAP | 30 | 90 |
| | 22 | UDMA | 60 | DAP | 40 | 79 |
| | 23 | UDMA | 80 | BAC | 20 | 91 |
| | 24 | UDMA | 70 | BAC | 30 | 84 |
| | 25 | UDMA | 60 | BAC | 40 | 69 |
| | 26 | UDMA | 80 | DAC | 20 | 88 |
| | 27 | UDMA | 70 | DAC | 30 | 76 |
| | 28 | UDMA | 60 | DAC | 40 | 68 |
| Comparative Example | 9 | UDMA | 80 | DVB | 20 | 14 |
| | 10 | UDMA | 80 | TEGDMA | 20 | 64 |
| | 11 | UDMA | 70 | TEGDMA | 30 | 60 |
| | 12 | UDMA | 60 | TEGDMA | 40 | 59 |

It can be understood that molded bodies obtained by photo-curing the polymerizable composition of the present invention for a dental material exhibited higher degree of polymerization than molded bodies obtained by curing a conventional polymerizable composition for a dental material. That is, use of a compound including an allyl group as a diluting monomer provides polymerization-promoting effect. This is expected to lead to enhancement of flexural strength and breaking energy for polymerizable compositions for a dental material.

The invention claimed is:

1. A polymerizable composition for a dental material, the polymerizable composition comprising:
   one selected from the group consisting of allyl compound (A) and an oligomer of allyl compound (A),
   (meth)acrylate compound (B), and
   optionally a polymerization initiator,
   wherein the allyl compound (A) includes compound (A1) represented by general formula (A1) below or compound (A2) represented by general formula (A2) below:

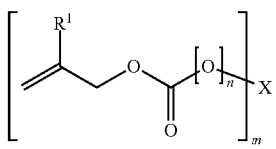

(A1)

wherein m is an integer of 2 to 8, each group $R^1$ is a hydrogen atom or a methyl group, groups $R^1$ are the same or different, n is an integer of 0 or 1, X is an m-valent $C_{2-100}$ hydrocarbon group optionally having a substituent and optionally containing a heteroatom,

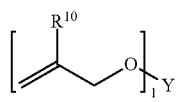

(A2)

wherein l is an integer of 1 to 8, each group $R^{10}$ is a hydrogen atom or a methyl group, groups $R^{10}$ are the same or different;

if l is 2 to 8, then Y is an l-valent $C_{2-100}$ hydrocarbon group optionally having a substituent and optionally containing a heteroatom, and if l is 1, then Y is a group represented by general formula (Y1) below:

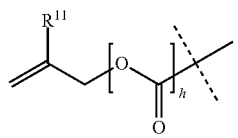

(Y1)

wherein $R^{11}$ is a hydrogen atom or a methyl group, h is an integer of 0 or 1, and the dashed line part represents a bonding position to the group in the parentheses in formula (A2), wherein the polymerization initiator comprises at least one selected from a room-temperature polymerization initiator, a thermal polymerization initiator and a photopolymerization initiator, the room-temperature polymerization initiator is at least one selected from an organic peroxide/amine systems, a cumene hydroperoxide/thiourea system, an ascorbic acid/$Cu^{2+}$ salt system, an organic peroxide/amine/sulfinic acid, tributylborane, and organic sulfinic acid, the thermal polymerization initiator is at least one selected from a peroxide and an azo compound.

2. The polymerizable composition for a dental material according to claim 1, wherein a mass ratio of allyl compound (A) to (meth)acrylate compound (B) is in a range of 0.05 or higher and lower than 1.0.

3. The polymerizable composition for a dental material according to claim 1, wherein allyl compound (A) is a compound having an allyloxy group.

4. The polymerizable composition for a dental material according to claim 1, wherein allyl compound (A) includes compound (A1) represented by general formula (A1), and X in general formula (A1) is an m-valent $C_{2-100}$ chain hydrocarbon group optionally having a substituent and optionally containing a heteroatom, an m-valent $C_{5-16}$ alicyclic hydrocarbon group optionally having a substituent and optionally containing a heteroatom, or an m-valent $C_{6-50}$ aromatic hydrocarbon group optionally having a substituent and optionally containing a heteroatom.

5. The polymerizable composition for a dental material according to claim 1, wherein allyl compound (A) includes compound (A1) represented by general formula (A1), and X in general formula (A1) is a group represented by any of general formulas (X1) to (X12) below:

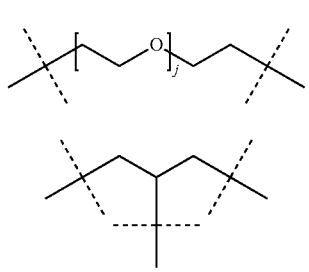

(X1)

(X2)

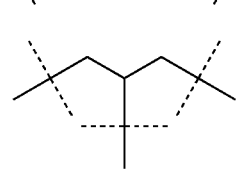

(X3)

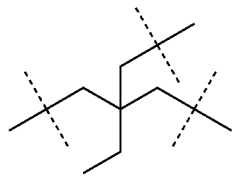

(X4)

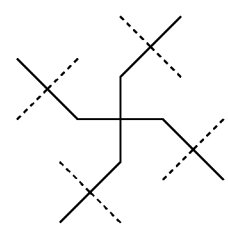

(X5)

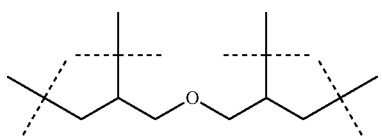

(X6)

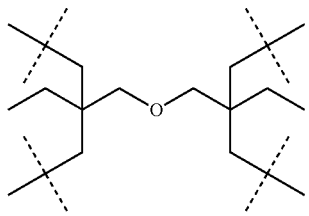

(X7)

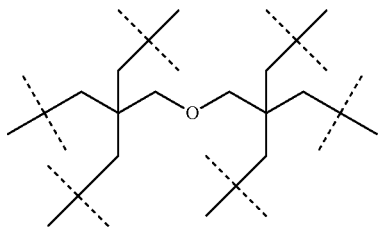

-continued (X8)
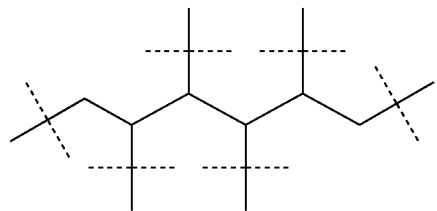

(X9)
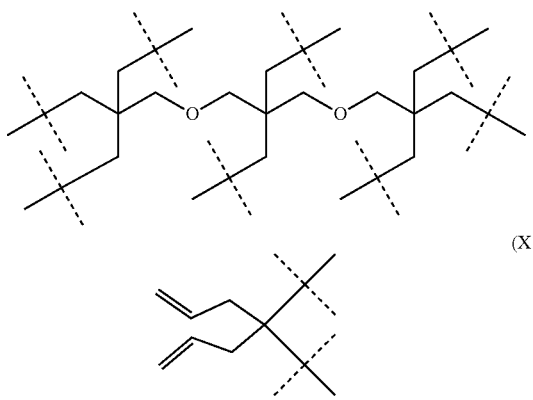

(X10)
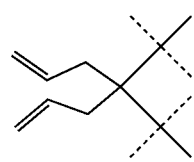

(X11)
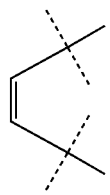

(X12)
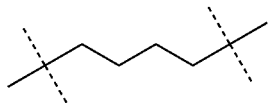

wherein j is an integer of 1 to 50, and each dashed line part in formulas (X1) to (X12) represents a bonding position to the group in the parentheses in formula (A1).

6. The polymerizable composition for a dental material according to claim 1, wherein allyl compound (A) includes compound (A1) represented by general formula (A1), and X in general formula (A1) is an m-valent $C_{5-16}$ alicyclic hydrocarbon group optionally having a substituent and optionally containing a heteroatom.

7. The polymerizable composition for a dental material according to claim 1, wherein allyl compound (A) includes compound (A1) represented by general formula (A1), and X in general formula (A1) is a group represented by any of general formulas (X13) to (X16) below:

(X13)
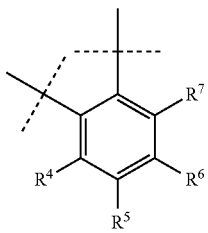 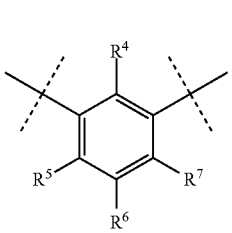

-continued

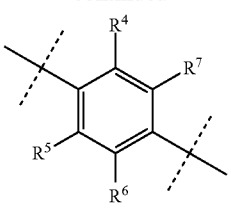

(X14)
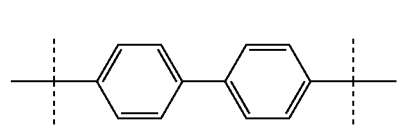

(X15)
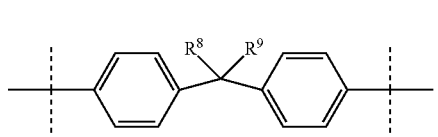

(X16)
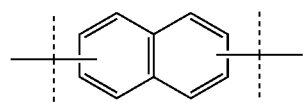

wherein each dashed line part represents a bonding position to the group in the parentheses in formula (A1); $R^4$ to $R^7$ in formula (X13) are each independently a hydrogen atom, a halogen atom, or a $C_{1-20}$ aliphatic hydrocarbon group optionally containing a heteroatom, and the two dashed-lined bonding sites on the benzene ring are in any of ortho relationship, meta relationship, and para relationship; $R^8$ and $R^9$ in formula (X15) are each independently a hydrogen atom or a methyl group; and each of the two dashed-lined bonding sites on the naphthalene ring in formula (X16) is present at any of the eight bondable positions, and hydrogen atoms at positions other than the dashed-lined bonding sites on the naphthalene ring are each optionally replaced with another group.

8. The polymerizable composition for a dental material according to claim 1, wherein allyl compound (A) includes compound (A2) represented by general formula (A2), and Y in general formula (A2) is an l-valent $C_{2-20}$ chain hydrocarbon group optionally having a substituent and optionally containing a heteroatom.

9. The polymerizable composition for a dental material according to claim 1, wherein allyl compound (A) includes compound (A2) represented by general formula (A2), and Y in general formula (A2) is a group represented by general formula (Y1) or a group represented by any of general formulas (Y2) to (Y5) below:

(Y2)
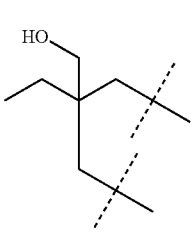

(Y3) 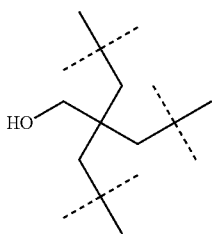

(Y4) 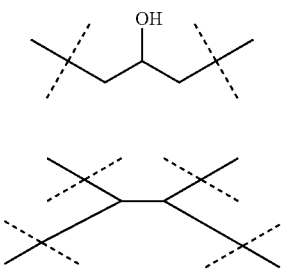

(Y5)

wherein each dashed line part represents a bonding position to the group in the parentheses in formula (A2).

10. The polymerizable composition for a dental material according to claim 1, wherein (meth)acrylate compound (B) includes (meth)acrylate compound (B-a) represented by general formula (2) below:

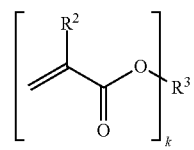

(2)

wherein k is an integer of 2 to 4, $R^3$ is a k-valent hydrocarbon group optionally having a heteroatom, and $R^2$ is a hydrogen atom or a methyl group.

11. The polymerizable composition for a dental material according to claim 1, the polymerizable composition further comprising a polymerization initiator.

12. The polymerizable composition for a dental material according to claim 11, wherein the polymerization initiator contains a photopolymerization initiator.

13. The polymerizable composition for a dental material according to claim 1, the polymerizable composition further comprising a filler.

14. The polymerizable composition for a dental material according to claim 1, wherein a viscosity of the polymerizable composition for a dental material at 65° C. is 1 to 300,000 mPa·s.

15. The polymerizable composition for a dental material according to claim 1, wherein the polymerizable composition is used as a dental composite resin.

16. A molded body obtained by curing the polymerizable composition for a dental material according to claim 1.

17. A dental material comprising the molded body according to claim 16.

* * * * *